US009055745B2

(12) United States Patent
James-Meyer et al.

(10) Patent No.: US 9,055,745 B2
(45) Date of Patent: Jun. 16, 2015

(54) COMPOSITIONS FOR INTERNAL AND EXTERNAL INSECTICIDES, OVICIDES, REPELLENTS AND WOUND HEALING

(75) Inventors: Lynn S. James-Meyer, Denison, TX (US); Gerald C. Coles, Bristol (GB)

(73) Assignee: Natureza, Inc., Denison, TX (US)

( * ) Notice: Subject to any disclaimer, the term of this patent is extended or adjusted under 35 U.S.C. 154(b) by 0 days.

(21) Appl. No.: 14/007,221

(22) PCT Filed: Apr. 13, 2012

(86) PCT No.: PCT/US2012/033580
§ 371 (c)(1),
(2), (4) Date: Sep. 24, 2013

(87) PCT Pub. No.: WO2012/142452
PCT Pub. Date: Oct. 18, 2012

(65) Prior Publication Data
US 2014/0018434 A1    Jan. 16, 2014

Related U.S. Application Data

(60) Provisional application No. 61/517,140, filed on Apr. 13, 2011.

(51) Int. Cl.
*A61K 31/164* (2006.01)
*A01N 37/20* (2006.01)
*A01N 37/02* (2006.01)
*A01N 37/18* (2006.01)

(52) U.S. Cl.
CPC ............... *A01N 37/20* (2013.01); *A01N 37/02* (2013.01); *A01N 37/18* (2013.01); *A61K 31/164* (2013.01)

(58) Field of Classification Search
CPC ................................... A61K 31/164
USPC ........................................ 514/625
See application file for complete search history.

(56) References Cited

U.S. PATENT DOCUMENTS

| 3,670,080 A | 6/1972 | Hirata |
| 4,185,027 A | 1/1980 | Logan |
| 4,430,245 A | 2/1984 | Beattie |
| 4,689,083 A | 8/1987 | Gutmann et al. |
| 5,108,661 A | 4/1992 | Boiteux et al. |
| 5,238,933 A | 8/1993 | Catz et al. |
| 5,462,736 A | 10/1995 | Rech et al. |
| 5,496,857 A | 3/1996 | Targosz |
| 5,573,700 A | 11/1996 | Steltenkamp et al. |
| 5,589,181 A | 12/1996 | Bencsits |
| 5,620,695 A | 4/1997 | Elliott |
| 5,716,627 A | 2/1998 | Granger et al. |
| 5,776,475 A | 7/1998 | Kilpatrick-Liverman et al. |
| 5,814,310 A | 9/1998 | Nagy et al. |
| 5,925,615 A | 7/1999 | Kern et al. |
| 5,962,012 A | 10/1999 | Lin et al. |
| 5,968,498 A | 10/1999 | Okada et al. |
| 5,977,023 A | 11/1999 | Inoue et al. |
| 5,998,475 A | 12/1999 | James et al. |
| 6,093,681 A | 7/2000 | Ward et al. |
| 6,103,768 A | 8/2000 | Savage et al. |
| 6,133,199 A | 10/2000 | Soula et al. |
| 6,139,866 A | 10/2000 | Chono et al. |
| 6,204,230 B1 | 3/2001 | Taylor et al. |
| 6,255,253 B1 | 7/2001 | Foerster et al. |
| 6,475,953 B1 | 11/2002 | Ward et al. |
| 6,479,434 B1 | 11/2002 | Gillespie et al. |
| 6,555,515 B1 | 4/2003 | Hees et al. |
| 6,596,763 B1 | 7/2003 | Thormar et al. |
| 6,602,838 B1 | 8/2003 | Koester et al. |
| 6,607,716 B1 | 8/2003 | Smith et al. |
| 6,755,201 B1 | 6/2004 | Kosboth et al. |
| 6,821,523 B2 | 11/2004 | Maibach et al. |
| 6,846,796 B2 | 1/2005 | Schmid |
| 6,846,837 B2 | 1/2005 | Maibach et al. |

(Continued)

FOREIGN PATENT DOCUMENTS

DE    4424210 A1    1/1996
DE    10216509 A1    10/2003

(Continued)

OTHER PUBLICATIONS

International Search Report and Written Opinion in PCT Patent Application No. PCT/US2012/033580 dated Jul. 6, 2012 (13 pages).
Farag, Mohamad, et al. Repellent and Insecticidal Activities of *Melia azedarach* L. against Cotton Leafworm, *Spodoptera littoralis* (Boisd.), Z. Naturforsch. 66c 129-135 (2011).
Tebayashi, Shin-ichi, Feeding Stimulants Eleciting the Proving Behavior for *Peregrinator biannulipes* Montrouzier et Signore (Hemiptera: Ruduviidae) from *Tribolium confusum* (Jacquelin du Val); Z. Naturforsch. 58c, 295-299 (2003).

(Continued)

*Primary Examiner* — Shirley V Gembeh
(74) *Attorney, Agent, or Firm* — Gardere Wynne Sewell LLP

(57) ABSTRACT

Exemplary embodiments of the present invention relate to pesticides, insecticides, insect repellant, insect anti-feeding, cleaning, glue dissolving and anti-irritation and wound healing compositions for humans and animals and, more particularly, to such compositions which are effective in killing, removing and/or repelling a wide range of endoparasites, ectoparasites and insects while also being non-toxic to humans, animals, and the environment. An exemplary embodiment of the present invention is directed to an aqueous composition including a mixture of at least one ethanolamide and at least one esterified fatty acid. Another exemplary embodiment of the present invention is directed to an aqueous composition including at least one esterified fatty acid in water and at least one emulsifier. The aqueous compositions may be used as a cleaning composition, insecticide, insect repellant, glue solvent or to relieve irritation from and/or promote healing of insect bites, skin abrasions superficial burns and wounds.

34 Claims, 12 Drawing Sheets

(56) References Cited

U.S. PATENT DOCUMENTS

| | | |
|---|---|---|
| 6,861,397 B2 | 3/2005 | Seitz, Jr. et al. |
| 6,919,076 B1 | 7/2005 | Green et al. |
| 6,943,197 B2 | 9/2005 | Maibach et al. |
| 6,958,148 B1 | 10/2005 | Green et al. |
| 6,977,082 B2 | 12/2005 | Seitz, Jr. et al. |
| 7,718,188 B2 | 5/2010 | Ito et al. |
| 7,785,622 B2 | 8/2010 | Ito et al. |
| 8,084,395 B2 | 12/2011 | Selles et al. |
| 8,133,847 B2 | 3/2012 | Carter et al. |
| 8,137,715 B2 | 3/2012 | Shah et al. |
| 2001/0018043 A1 | 8/2001 | Henning et al. |
| 2002/0172646 A1 | 11/2002 | Weipert et al. |
| 2004/0115152 A1 | 6/2004 | Hannich et al. |
| 2004/0127553 A1 | 7/2004 | Hallahan |
| 2005/0232891 A1 | 10/2005 | Moloney et al. |
| 2007/0129253 A1 | 6/2007 | Hailu et al. |
| 2008/0280978 A1 | 11/2008 | Zeelie et al. |
| 2009/0068255 A1 | 3/2009 | Yu et al. |
| 2009/0130739 A1 | 5/2009 | Burke et al. |
| 2010/0227010 A1* | 9/2010 | Jones ............................ 424/747 |
| 2010/0331377 A1 | 12/2010 | McCord |
| 2011/0172211 A1 | 7/2011 | Baek et al. |

FOREIGN PATENT DOCUMENTS

| | | |
|---|---|---|
| EP | 1787514 A1 | 5/2007 |
| GB | 768129 A | 2/1957 |
| JP | 11001404 | 6/1999 |
| JP | 2003020496 A | 1/2003 |
| WO | WO-9624328 A1 | 8/1996 |
| WO | WO-03095600 A1 | 11/2003 |
| WO | WO-2004006674 A1 | 1/2004 |
| WO | WO-2009012785 A2 | 1/2009 |

OTHER PUBLICATIONS

Supplementary Extended Search Report for European Patent Application No. 12771587.8 dated Sep. 12, 2014 (8 pages).

Machine translation obtained from EPO/Google for DE10216509 (33 pages). (2003).

Translation of Japanese Publication No. JP 11-001404, Application No. JP19970169427 (7 pages). (1997).

WPI/Thomson Database Acquisition XP 002729123 of JP Applicaton No. 19970169427, Japanese Publication No. JP 11-001404, published Jan. 6, 1999 (3 pages).

* cited by examiner

Average number of flies Front legs – Treated Group

Average number of flies Front legs – Control Group daily number of flies on each animal

| Treatment animal | 0 | 24h | 48h | 72h | 96h |
|---|---|---|---|---|---|
| 40 | 20 | 1 | 11 | 19 | 6 |
| 39 | 0 | 0 | 11 | 45 | 0 |
| 16 | 14 | 6 | 0 | 9 | 19 |
| 2509 | 7 | 13 | 11 | 16 | 15 |
| 318 | 35 | 6 | 16 | 14 | 36 |
| 34 | 12 | 2 | 14 | 10 | 2 |

| Control animal | 0 | 24h | 48h | 72h | 96h |
|---|---|---|---|---|---|
| 33 | 15 | 15 | 9 | 9 | 15 |
| 41 | 10 | 9 | 6 | 5 | 17 |
| 38 | 5 | 31 | 6 | 5 | 3 |
| 42 | 0 | 26 | 25 | 14 | 36 |
| 2501 | 46 | 7 | 43 | 8 | 19 |
| 2492 | 4 | 11 | 18 | 31 | 18 |

| Efficacy | % |
|---|---|
| 24h | 71% |
| 48h | 35% |
| 72h | 0 |
| 96h | 30% |

FIG. 6

Average number of flies Back legs – Treated Group

Average number of flies Back legs – Control Group

Efficacy of Treatment Composition on *Musca domestica*

| Evaluation Time | 24h | 48h | 72h | 96h |
|---|---|---|---|---|
| Front Legs | 0 | 15 | 0 | 3 |
| Back Legs | 48 | 77 | 48 | 28 |

FIG. 9

Treatment applyed on front legs of Dairy Cows

| treatment animal | 0 24h | 48h | 72h | 96h | |
|---|---|---|---|---|---|
| 40 | 20 | 1 | 11 | 19 | 6 |
| 39 | 0 | 0 | 11 | | 0 |
| 16 | 14 | 6 | 0 | 9 | 19 |
| 2509 | 7 | 13 | 11 | 16 | 15 |
| 318 | 35 | 6 | 16 | 14 | 36 |
| 34 | 12 | 2 | 14 | 10 | 2 |
| | 14.7 | 4.7 | 10.5 | 13.6 | 13.0 |

| control animal | 0 24h | 48h | 72h | 96h | |
|---|---|---|---|---|---|
| 33 | 15 | 15 | 9 | 9 | 15 |
| 41 | 10 | 9 | 6 | 5 | 17 |
| 38 | 5 | 31 | 6 | 5 | 3 |
| 42 | 0 | 26 | 25 | 14 | 36 |
| 2501 | 46 | 7 | 43 | 8 | 19 |
| 2492 | 4 | 11 | 18 | 31 | 18 |
| | 13.3 | 16.5 | 17.8 | 12.0 | 18.0 |

| Efficacy | % |
|---|---|
| 24h | 71% |
| 48h | 35% |
| 72h | 0 |
| 96h | 30% |

FIG. 10

Number of flies on front legs of dairy cows – Solid line=control, dashed line=treatment

| | Summary of Test | | | |
|---|---|---|---|---|
| | Agar Migration Test - Treatment Composition Sheep | | | |
| Conc. | Day 1 | Day 2 | Day 3 | Average Number of Larvae |
| 300 μL | 1 | 2 | 0 | 1 |
| 150 μL | 6 | 9 | 8 | 7.666666667 |
| 75 μL | 6 | 14 | 29 | 16.33333333 |
| 40 μL | 51 | 69 | 100 | 73.33333333 |
| 20 μL | 126 | 45 | 111 | 94 |
| 10 μL | 143 | 137 | 155 | 145 |
| 5 μl | 147 | 148 | 210 | 168.3333333 |
| Control | 538 | 520 | 441 | 499.6666667 |

COMPOSITIONS FOR INTERNAL AND EXTERNAL INSECTICIDES, OVICIDES, REPELLENTS AND WOUND HEALING

CROSS-REFERENCE TO RELATED APPLICATIONS

This application claims priority to U.S. Provisional Appl. No. 61/517,140 filed Apr. 13, 2011, which is hereby incorporated by reference in its entirety.

BACKGROUND OF THE INVENTION

1. Technical Field

This invention relates to pesticides, insecticides, insect repellant, insect anti-feeding, cleaning, glue dissolving and anti-irritation and wound healing compositions for humans and animals and, more particularly, to such compositions which are effective in killing, removing and/or repelling a wide range of endoparasites, ectoparasites and insects while also being non-toxic to humans, animals, and the environment.

2. Background of the Invention

There is a need for products that are effective at controlling, killing, removing and/or repelling insects, for example blood-sucking insects, such as mosquitoes, ticks, fleas, lice, bed bugs, tsetse flies and other nuisance insects. For example in the treatment of human head lice, there is a need for a product that is capable of killing all lice in a single treatment, removes nits, is easy to apply, has a short treatment time, provides protection from reinfestation, is gentle to the scalp and other skin area to which it comes into contact with, is non-damaging to hair, is non-toxic to humans, is easy to remove and does not provide a lingering odor. It is also desirable that there is little or no risk of development of resistance to the product, for example such a problem of resistance has been observed with pyrethroids and malathion. These products have a specific target site action, and mutation and therefore development of resistance is possible. In addition, malathion products have a 8 to 12 hour treatment time, which is not very convenient for a user. Accordingly, it is desirable for a product to have a mechanical mode of action in order to reduce the likelihood of developing resistance by the insects and/or pests that are intended to be controlled, killed, removed and/or repelled by the product. What is needed is a product that overcomes the deficiencies in the prior treatment compositions, and addresses the requirements for products that are used in the controlling, killing, removing and/or repelling of insects and/or other pests.

SUMMARY OF THE INVENTION

The present invention is designed to overcome the above noted limitations that are attendant upon the use of conventional insecticides and pesticides and, toward this end, it contemplates the provision of aqueous compositions that are effective in killing, removing and/or repelling a wide range of insects while also being non-toxic to humans, animals, and the environment.

It is an object of the present invention to provide compositions that are effective at controlling, killing, removing and/or repelling insects and other pests, such as head lice.

It is another object of the present invention that such compositions are effective at killing and/or removing head lice nits from hair.

It is still another object the present invention that such compositions have a short application time.

It is yet a further object of the present invention that such compositions can be in the form a cosmetically elegant shampoo, for example odor free, drip free and easy to rinse.

It is yet a further object of the present invention that such compositions can be used routinely in order to control new infestation.

It is yet another object of the present invention that such compositions are gentle and have beneficial effects on the skin.

It is yet another object of the present invention that such compositions may be used as a glue solvent and/or glue dissolver for a variety of types of glues and adhesives, and more particularly the glue produced by head lice that hold their eggs on hair.

It is yet another object of the present invention that such compositions are capable of relieving irritation from insect bites and skin abrasions.

It is yet another object of the present invention that such compositions may be used for aiding in the healing of scratches, cuts, abrasions and burns to promote faster healing and less scarring.

It is still another object of the present invention that such compositions may be used as a spot on treatment for animals against fleas, mites, ticks and other biting insects.

It is yet another object of the present invention that such compositions may be used as an anti-parasitic treatment to both endoparasites and ectoparasites. For example, such compositions may be used against infective gastrointestinal protozoa, such as coccidian and cryptosporidium.

It is still another object of the present invention that such compositions may be used against infections and/or irritations caused by bacteria, protozoa pathogens, fungi and virus of humans, animals and plants when applied externally or taken internally.

It is another object of the present invention that such compositions may be used as cleaning compounds, especially for the removal of glues and paints.

An exemplary embodiment of the present invention is directed to an aqueous composition including a mixture of at least one amide, for example at least one ethanolamide, and more particularly diethanolamide, and at least one esterified fatty acid, for example a fatty acid methyl ester, that may be used as a cleaning composition, insecticide, insect repellant, glue solvent or to relieve irritation from and/or promote healing of insect bites, skin abrasions superficial burns and wounds. The fatty acid methyl esters may include the short chain esters, branched chain acids and uneven acids, for example methyl esters of C9, C11, C13, C15 in chain lengths C8 to C18, and the fatty acid methyl esters may further include all fatty acids of methyl esters between C8 and C18. Most efficacious are the methyl and ethyl esters, particularly lauric acid methyl ester, propyl and isopropyl esters. The aqueous composition may also include polyethylene glycol, one or more surfactants and/or detergents, one or more alcohols, one or more preservatives and one or more buffering agents. The aqueous composition may also include one or more stabilizers and/or one or more conditioning agents. The aqueous composition may be in the form of a shampoo, a lotion, a spray shampoo, a gel or a spray repellant.

Another exemplary embodiment of the present invention is directed to an aqueous composition including at least one esterified fatty acid, for example a fatty acid methyl ester, water and at least one emulsifier. The aqueous composition may be used as a cleaning composition, insecticide, insect repellant, glue solvent or to relieve irritation from and/or promote healing of insect bites, skin abrasions superficial burns and wounds. An example of at least one fatty acid methyl ester is any fatty acid methyl ester between C8 and C18, such as lauric acid methyl ester, caprylic acid methyl ester, capric acid methyl ester, myristic acid methyl ester, palmitic acid methyl ester, stearic acid methyl ester, unsaturated oleic acid methyl ester or mixtures thereof. The at least one esterified fatty acid used in the aqueous composition may also be a fatty acid ethyl ester, a fatty acid propyl ester or a fatty acid isopropyl ester. It is understood that the at least one esterified fatty acid may be a blend of one or more of a fatty acid methyl ester, a fatty acid ethyl ester, a fatty acid propyl ester and/or a fatty acid isopropyl ester. For example, ethyl esters of different chain lengths of the fatty acids and particularly methyl, ethyl, propyl and isopropyl esters of lauric acid or mixtures thereof may be used in the aqueous composition. Examples of ethyl, propyl and isopropyl fatty acid esters that may also be used in the aqueous composition include esters of lauric acid, caprylic acid, capric acid, myristic acid, palmitic acid, stearic acid, unsaturated oleic acid or mixtures thereof. The aqueous composition may also include at least one alcohol, for example ethanol. Furthermore, the aqueous composition may also include at least one fragrance and/or at least one preservative.

While it is understood that the present invention is directed to aqueous compositions including fatty acid methyl esters and ethanolamides. It should also be understood that the aqueous compositions including only esterified fatty acid, such as fatty acid methyl, ethyl and isopropyl esters in the C8 to C18 ranges have at least equal efficacy for at least the uses mentioned above than compositions including only fatty acids and ethanolamides, and much better efficacy than compositions including just plain fatty acids.

An exemplary embodiment of the present invention is directed to a composition that includes at least one amide, at least one esterified fatty acid, and water. The at least one amide of the composition may include diethanolamide, the at least one esterified fatty acid includes at least one esterified fatty acid from a coconut oil. A concentration of at least one amide in the composition is at least 80% by weight based upon the weight of the total composition, a concentration of the at least one esterified fatty acid in the composition is between 8-15% by weight based upon the weight of the total composition, and a concentration of a free amine radical in the composition is 1.5% or less by weight based upon the weight of the total composition.

In accordance with the exemplary embodiment of the present invention, the at least one esterified fatty acid from the coconut oil is a fatty acid methyl ester, and the fatty acid methyl ester may be any one of lauric acid methyl ester, oleic acid methyl ester, palmitic acid methyl ester, myristic acid methyl ester, linoleic acid methyl ester, stearic acid methyl ester or mixtures thereof.

In accordance with the exemplary embodiment of the present invention, the composition may be configured for use in aiding in the healing of scratches, cuts, abrasions and burns.

Another exemplary embodiment of the present invention is directed to a composition that includes between 10-60% of water by weight based upon the weight of the total composition, between 5-50% of a mixture by weight based upon the weight of the total composition, wherein the mixture comprises diethanolamide and at least one esterified fatty acid, between 2-50% of polyethylene glycol by weight based upon the weight of the total composition, between 5-50% of at least one surfactant by weight based upon the weight of the total composition, between 5-35% of at least one alcohol by weight based upon the weight of the total composition, between 0.1-5% of at least one preservative by weight based upon the weight of the total composition, and at least one buffering agent.

In accordance with the exemplary embodiment of the present invention, the at least one esterified fatty acid of the mixture comprises at least one esterified fatty acid from a coconut oil, a concentration of diethanolamide in the mixture is at least 80% by weight based upon the weight of the total mixture, a concentration of the at least one esterified fatty acid in the mixture is between 8-15% by weight based upon the weight of the total mixture, and a concentration of a free amine radical in the mixture is 1.5% or less by weight based upon the weight of the total mixture.

In accordance with the exemplary embodiment of the present invention, the composition may also include at least one stabilizer, and at least one conditioning agent.

In accordance with the exemplary embodiment of the present invention, the composition may be a shampoo, and the shampoo is configured for use in treatment or removal of blood sucking insects by applying the shampoo to dry hair.

In accordance with the exemplary embodiment of the present invention, the mixture in the composition includes coconut diethanolamide.

In accordance with the exemplary embodiment of the present invention, the composition more particularly includes about 25% by weight of water, about 30% by weight of the mixture and about 30% by weight of polyethylene glycol by weight based upon the weight of the total composition, and the at least one surfactant includes sodium methyl cocoyl taurate and sodium laureth sulfate, and the sodium methyl cocoyl taurate comprises about 6% by weight of the composition based upon the weight of the total composition and the sodium laureth sulfate comprises about 2% by weight of the composition based upon the weight of the total composition.

In accordance with the exemplary embodiment of the present invention, the at least one alcohol comprises propanediol, and the propanediol comprises about 5% by weight of the composition based upon the weight of the total composition, the at least one preservative comprises cocamidopropyl PG dimonium chloride phosphate, and cocamidopropyl PG dimonium chloride phosphate comprises about 1% by weight of the composition based upon the weight of the total composition, and the at least one buffering agent comprises citric acid, and the citric acid comprises about 1% by weight of the composition based upon the weight of the total composition.

In accordance with the exemplary embodiment of the present invention, the at least one esterified fatty acid from the coconut oil is a fatty acid methyl ester, and the fatty acid methyl ester may be any one of lauric acid methyl ester, oleic acid methyl ester, palmitic acid methyl ester, myristic acid methyl ester, linoleic acid methyl ester, stearic acid methyl ester or mixtures thereof.

In accordance with the exemplary embodiment of the present invention, the polyethylene glycol may be any one of octaethylene glycol, PEG-6, glyceryl ether benzoate, isobudecyl ether, glyceryl ether lactate, PEG-10, PEG-19, PEG-20 or mixtures thereof, the at least one surfactant may be any one of sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate or mixtures thereof, the at least one alcohol may be any one of ethanol, propandiol, pentylene glycol, propylene glycol, butylene glycol, benzyl alcohol, isopropanol or mixtures thereof; the at least one buffering agent may be any one of citric acid, lactic acid, phosphoric acid, sodium hydroxide, triethanolamine or mixtures thereof, the at least one preservative may be any one of cocamidopropyl PG dimonium chloride phosphate, sorbic acid, methylparaben, phenoxyethanol, chlorphenesin, potassium sorbate, sodium benzoate, sodium alginate or mixtures thereof.

Another exemplary embodiment of the present invention is directed to a composition that includes between 10-60% of water by weight based upon the weight of the total composition, between 5-50% of a mixture by weight based upon the weight of the total composition, wherein the mixture comprises diethanolamide and at least one esterified fatty acid, between 5-50% of polyethylene glycol by weight based upon the weight of the total composition, between 5-50% of at least one surfactant by weight based upon the weight of the total composition, between 5-35% of at least one alcohol by weight based upon the weight of the total composition, between 0.1-5% of at least one preservative by weight based upon the weight of the total composition, and at least one buffering agent.

In accordance with the exemplary embodiment of the present invention, the at least one esterified fatty acid of the mixture comprises at least one esterified fatty acid from a coconut oil, a concentration of diethanolamide in the mixture is at least 80% by weight based upon the weight of the total mixture, a concentration of the at least one esterified fatty acid in the mixture is between 8-15% by weight based upon the weight of the total mixture, and a concentration of a free amine radical in the mixture is 1.5% or less by weight based upon the weight of the total mixture.

In accordance with the exemplary embodiment of the present invention, the composition may also include at least one stabilizer, and at least one conditioning agent.

In accordance with the exemplary embodiment of the present invention, the at least one stabilizer may be any one of PEG-120 methyl glucose dioleate, Distearate-75 IPDI, xanthan gum, acadia gum or a mixture thereof, and the at least one conditioning agent may be any one of phenyl trimethicone, cetrimonium chloride, stearamidopropyl dymethylamine, hydrolyzed wheat protein, Polyquaternium-7 or mixtures thereof.

In accordance with the exemplary embodiment of the present invention, the composition may also include about 10% of a second alcohol by weight based upon the weight of the total composition, and between 1-5% of at least one emulsifier by weight based upon the weight of the total composition. The at least one stabilizer is between 2-6% by weight based upon the weight of the total composition, and the at least one conditioning agent is between 2-6% by weight based upon the weight of the total composition.

In accordance with the exemplary embodiment of the present invention, the second alcohol may be any one of benzyl alcohol, ethanol, isopropanol or mixtures thereof, and the at least one emulsifier may be any one of polysorbate 20, disodium cetearyl sulfosuccinamate or mixtures thereof.

In accordance with the exemplary embodiment of the present invention, the composition may further include 0.5% or less by weight based upon the weight of the total composition of at least one fragrance, and 0.5% or less by weight based upon the weight of the total composition of at least one coloring agent.

In accordance with the exemplary embodiment of the present invention, the composition may be a spray shampoo, and the spray shampoo is configured for use in treatment or removal of blood sucking insects.

In accordance with the exemplary embodiment of the present invention, the mixture in the composition includes coconut diethanolamide.

In accordance with the exemplary embodiment of the present invention, the at least one esterified fatty acid from the coconut oil is a fatty acid methyl ester, and the fatty acid methyl ester may be any one of lauric acid methyl ester, oleic acid methyl ester, palmitic acid methyl ester, myristic acid methyl ester, linoleic acid methyl ester, stearic acid methyl ester or mixtures thereof.

In accordance with the exemplary embodiment of the present invention, the polyethylene glycol may be any one of octaethylene glycol, PEG-6, glyceryl ether benzoate, isobudecyl ether, glyceryl ether lactate, PEG-10, PEG-19, PEG-20 or mixtures thereof, the at least one surfactant may be any one of sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate or mixtures thereof, the at least one alcohol may be any one of ethanol, propandiol, pentylene glycol, propylene glycol, butylene glycol, benzyl alcohol or isopropanol or mixtures thereof, the at least one buffering agent may be any one of citric acid, lactic acid, phosphoric acid, sodium hydroxide, triethanolamine or mixtures thereof, the at least one preservative may be any one of cocamidopropyl PG dimonium chloride phosphate, sorbic acid, methylparaben, phenoxyethanol, chlorphenesin, potassium sorbate, sodium benzoate, sodium alginate or mixtures thereof, the at least one stabilizer may be any one of PEG-120 methyl glucose dioleate, Distearate-75 IPDI, xanthan gum, acadia gum or mixtures thereof, and the at least one conditioning agent may be any one of phenyl trimethicone, cetrimonium chloride, stearamidopropyl dymethylamine, hydrolyzed wheat protein, Polyquaternium-7 or mixtures thereof.

Another exemplary embodiment of the present invention is directed to a composition that includes between 10-60% of water by weight based upon the weight of the total composition, between 5-50% of a mixture by weight based upon the weight of the total composition, wherein the mixture comprises diethanolamide and at least one esterified fatty acid, between 5-50% of polyethylene glycol by weight based upon the weight of the total composition, between 5-50% of at least one surfactant by weight based upon the weight of the total composition, between 5-35% of at least one alcohol by weight based upon the weight of the total composition, between 0.1-5% of at least one preservative by weight based upon the weight of the total composition, and at least one buffering agent.

In accordance with the exemplary embodiment of the present invention, the at least one esterified fatty acid of the mixture comprises at least one esterified fatty acid from a coconut oil, a concentration of diethanolamide in the mixture is at least 80% by weight based upon the weight of the total mixture, a concentration of the at least one esterified fatty acid in the mixture is between 8-15% by weight based upon the weight of the total mixture, and a concentration of a free amine radical in the mixture is 1.5% or less by weight based upon the weight of the total mixture.

In accordance with the exemplary embodiment of the present invention, the composition may also include at least one stabilizer, and at least one conditioning agent.

In accordance with the exemplary embodiment of the present invention, the composition may also include between 2-4% of acrylates copolymer by weight based upon the weight of the total composition, and between 2-6% of Polyquaternium-7 by weight based upon the weight of the total composition. The at least one stabilizer is between 2-6% by weight based upon the weight of the total composition, and the at least one conditioning agent is between 2-6% by weight based upon the weight of the total composition.

In accordance with the exemplary embodiment of the present invention, the composition may also include 0.5% or less by weight based upon the weight of the total composition of at least one fragrance, and 0.5% or less by weight based upon the weight of the total composition of at least one coloring agent.

In accordance with the exemplary embodiment of the present invention, the composition may be in a gel form, and the gel form is configured for use in treatment or removal of blood sucking insects.

In accordance with the exemplary embodiment of the present invention, the mixture in the composition includes coconut diethanolamide.

In accordance with the exemplary embodiment of the present invention, the at least one esterified fatty acid from the coconut oil is a fatty acid methyl ester, and the fatty acid methyl ester may be any one of lauric acid methyl ester, oleic acid methyl ester, palmitic acid methyl ester, myristic acid methyl ester, linoleic acid methyl ester, stearic acid methyl ester or mixtures thereof.

In accordance with the exemplary embodiment of the present invention, the polyethylene glycol may be any one of octaethylene glycol, PEG-6, glyceryl ether benzoate, isobudecyl ether, glyceryl ether lactate, PEG-10, PEG-19, PEG-20 or mixtures thereof, the at least one surfactant may be any one of sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate or mixtures thereof, the at least one alcohol may be any one of ethanol, propandiol, pentylene glycol, propylene glycol, butylene glycol, benzyl alcohol or isopropanol or mixtures thereof, the at least one buffering agent may be any one of citric acid, lactic acid, phosphoric acid, sodium hydroxide, triethanolamine or mixtures thereof, the at least one preservative may be any one of cocamidopropyl PG dimonium chloride phosphate, sorbic acid, methylparaben, phenoxyethanol, chlorphenesin, potassium sorbate, sodium benzoate, sodium alginate or mixtures thereof, the at least one stabilizer may be any one of PEG-120 methyl glucose dioleate, Distearate-75 IPDI, xanthan gum, acadia gum or mixtures thereof, and the at least one conditioning agent may be any one of phenyl trimethicone, cetrimonium chloride, stearamidopropyl dymethylamine, hydrolyzed wheat protein, Polyquaternium-7 or mixtures thereof.

Another exemplary embodiment of the present invention is directed to a spray repellant composition that may include between 10-70% of water by weight based upon the weight of the total composition, between 2-25% of a mixture by weight based upon the weight of the total composition, wherein the mixture comprises diethanolamide and at least one esterified fatty acid, about 5% of at least one stabilizer by weight based upon the weight of the total composition, at least one buffering agent, and between 0.1-0.5% of at least one fragrance by weight based upon the weight of the total composition.

In accordance with the exemplary embodiment of the present invention, the at least one esterified fatty acid of the mixture includes at least one esterified fatty acid from a coconut oil, a concentration of diethanolamide in the mixture is at least 80% by weight based upon the weight of the total mixture, a concentration of the at least one esterified fatty acid in the mixture is between 8-15% by weight based upon the weight of the total mixture, and wherein a concentration of a free amine radical in the mixture is 1.5% or less by weight based upon the weight of the total mixture.

In accordance with the exemplary embodiment of the present invention, the mixture in the spray repellant composition is coconut diethanolamide.

In accordance with the exemplary embodiment of the present invention, the at least one esterified fatty acid from the coconut oil is a fatty acid methyl ester, and wherein the fatty acid methyl ester may be any one of lauric acid methyl ester, oleic acid methyl ester, palmitic acid methyl ester, myristic acid methyl ester, linoleic acid methyl ester and stearic acid methyl ester.

In accordance with the exemplary embodiment of the present invention, the spray repellant composition is configured for use in repelling biting insects.

In accordance with the exemplary embodiment of the present invention, the at least one buffering agent may be any one of citric acid, lactic acid, phosphoric acid, sodium hydroxide, triethanolamine or mixtures thereof, and the at least one stabilizer may be any one of PEG-120 methyl glucose dioleate, Distearate-75 IPDI, xanthan gum, acadia gum or mixtures thereof.

Another exemplary embodiment of the present invention is directed to a composition that may include between 70-90% of water by weight based upon the weight of the total composition, between 2-20% of a mixture by weight based upon the weight of the total composition, the mixture may include diethanolamide and at least one esterified fatty acid, about 2% of cocamidepropyl PG dimonium chloride phosphate by weight based upon the weight of the total composition, about 1% of at least one buffering agent by weight based upon the weight of the total composition, between 2-5% of propanediol by weight based upon the weight of the total composition, and between 2-5% of at least one surfactant by weight based upon the weight of the total composition.

In accordance with the exemplary embodiment of the present invention, the at least one esterified fatty acid of the mixture comprises at least one esterified fatty acid from a coconut oil, a concentration of diethanolamide in the mixture is at least 80% by weight based upon the weight of the total mixture, a concentration of the at least one esterified fatty acid in the mixture is between 8-15% by weight based upon the weight of the total mixture, and a concentration of a free amine radical in the mixture is 1.5% or less by weight based upon the weight of the total mixture.

In accordance with the exemplary embodiment of the present invention, the at least one esterified fatty acid from the coconut oil is a fatty acid methyl ester, and wherein the fatty acid methyl ester may be any one of lauric acid methyl ester, oleic acid methyl ester, palmitic acid methyl ester, myristic acid methyl ester, linoleic acid methyl ester, stearic acid methyl ester and mixtures thereof.

In accordance with the exemplary embodiment of the present invention, the mixture in the composition may include coconut diethanolamide.

In accordance with the exemplary embodiment of the present invention, the composition may be configured for use in aiding in the healing of scratches, cuts, abrasions and burns.

In accordance with the exemplary embodiment of the present invention, the composition is configured for use in aiding in the treatment, repellance and/or killing of bed bugs, flies and/or fleas.

In accordance with the exemplary embodiment of the present invention, the composition is configured for use in effecting ovicidal activity on animal nematodes and *haemonchus*.

In accordance with the exemplary embodiment of the present invention, the at least one buffering agent may be any one of citric acid, lactic acid, phosphoric acid, sodium hydroxide, triethanolamine or mixtures thereof, the at least one surfactant may be any one of sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate or mixtures thereof, and the composition may also include comprises about 80% by weight of water, and about 2% by weight of the mixture based upon the weight of the total composition.

Another exemplary embodiment of the present invention is directed to a composition that may include between 65-95% of water by weight based upon the weight of the total composition, between 0.001-15% of at least one esterified fatty acid by weight based upon the weight of the total composition, and preferably 0.001-5% of the at least one esterified fatty acid by weight, and between 5-20% of at least one emulsifier by weight based upon the weight of the total composition.

In accordance with the exemplary embodiment of the present invention, the composition may also include between 0.1-30% of a mixture by weight based upon the weight of the total composition, the mixture may include diethanolamide and at least one coconut oil fatty acid methyl ester, a concentration of diethanolamide in the mixture is at least 80% by weight based upon the weight of the total mixture, a concentration of the at least one coconut oil fatty acid methyl ester in the mixture is between 8-15% by weight based upon the weight of the total mixture, a concentration of a free amine radical in the mixture is 1.5% or less by weight based upon the weight of the total mixture.

In accordance with the exemplary embodiment of the present invention, the mixture in the composition is coconut diethanolamide, and the at least one coconut oil fatty acid methyl ester may be any one of lauric acid methyl ester, oleic acid methyl ester, palmitic acid methyl ester, myristic acid methyl ester, linoleic acid methyl ester and stearic acid methyl ester or mixtures thereof.

In accordance with the exemplary embodiment of the present invention, the at least one esterified fatty acid may be any one of fatty acid methyl esters, fatty acid ethyl esters, fatty acid propyl esters and fatty acid isopropyl esters or mixtures thereof.

In accordance with the exemplary embodiment of the present invention, the at least one esterified fatty acid is a fatty acid of a methyl ester between C8 and C18 methyl esters or mixtures thereof.

In accordance with the exemplary embodiment of the present invention, the at least one esterified fatty acid may be any one of caprylic acid methyl ester, capric acid methyl ester, lauric acid methyl ester, myristic acid methyl ester, palmitic acid methyl ester, stearic acid methyl ester, unsaturated oleic acid methyl ester or mixtures thereof.

In accordance with the exemplary embodiment of the present invention, the composition may also include between 0.1-5% of at least one alcohol by weight based upon the weight of the total composition, and the at least one alcohol may include ethanol.

In accordance with the exemplary embodiment of the present invention, the composition may also include between 0.1-5% of at least one fragrance by weight based upon the weight of the total composition, between 0.1-5% of at least one preservative by weight based upon the weight of the total composition.

In accordance with the exemplary embodiment of the present invention, the at least one preservative may be any one of cocamidopropyl PG dimonium chloride phosphate, sorbic acid, methylparaben, phenoxyethanol, chlorphenesin, potassium sorbate, sodium benzoate, sodium alginate or mixtures thereof, and the at least one emulsifier may be any one of PEG-120 Methyl Glucose Dioleate, Distearate-75 IPDI, xanthan gum, acadia gum, polysorbate 20, disodium cetearyl sulfosuccinamate or mixtures thereof.

In accordance with the exemplary embodiment of the present invention, the composition may be configured for use as a pesticide, insecticide and/or insect repellant.

In accordance with the exemplary embodiment of the present invention, the composition may be configured for use as a cleaning, paint removing, insect residue removing and/or glue dissolving solution.

In accordance with the exemplary embodiment of the present invention, the composition may be configured for aiding in the healing of scratches, cuts, abrasions and burns.

In accordance with the exemplary embodiment of the present invention, the composition may be configured for use in killing, removing and/or repelling endoparasites and/or ectoparasites.

In accordance with the exemplary embodiment of the present invention, the composition is configured for use against infections and/or irritations caused by bacteria, protozoa pathogens, fungi and virus of humans, animals and plants.

Another exemplary embodiment of the present invention is directed to a composition that may include between 65-95% of water by weight based upon the weight of the total composition, between 0.001-15% of at least one esterified fatty acid by weight based upon the weight of the total composition, and preferably between 0.001-5% of the at least one esterified fatty acid by weight, between 5-20% of at least one emulsifier by weight based upon the weight of the total composition.

In accordance with the exemplary embodiment of the present invention, the at least one esterified fatty acid comprises lauric acid methyl ester.

In accordance with the exemplary embodiment of the present invention, the composition may also include between 0.1-5% of at least one alcohol by weight based upon the weight of the total composition, and the at least one alcohol may include ethanol.

In accordance with the exemplary embodiment of the present invention, the composition may also include between 0.1-5% of at least one fragrance by weight based upon the weight of the total composition, between 0.1-5% of at least one preservative by weight based upon the weight of the total composition.

In accordance with the exemplary embodiment of the present invention, the at least one preservative may be any one of cocamidopropyl PG dimonium chloride phosphate, sorbic acid, methylparaben, phenoxyethanol, chlorphenesin, potassium sorbate, sodium benzoate, sodium alginate or mixtures thereof, and the at least one emulsifier may be any one of PEG-120 Methyl Glucose Dioleate, Distearate-75 IPDI, xanthan gum, acadia gum, polysorbate 20, disodium cetearyl sulfosuccinamate or mixtures thereof.

In accordance with the exemplary embodiment of the present invention, the composition may be configured for use as a pesticide, insecticide and/or insect repellant.

In accordance with the exemplary embodiment of the present invention, the composition may be configured for use as a cleaning, paint removing, insect residue removing and/or glue dissolving solution.

In accordance with the exemplary embodiment of the present invention, the composition may be configured for aiding in the healing of scratches, cuts, abrasions and burns.

In accordance with the exemplary embodiment of the present invention, the composition may be configured for use in killing, removing and/or repelling endoparasites and/or ectoparasites.

In accordance with the exemplary embodiment of the present invention, the composition is configured for use against infections and/or irritations caused by bacteria, protozoa pathogens, fungi and virus of humans, animals and plants when applied externally or taken internally.

BRIEF DESCRIPTION OF THE FIGURE

FIG. 6 shows a table with the daily number of domestic flies on each animal in the Treatment and Control groups from FIG. 5;

FIG. 9 shows a pair of comparison tables showing the efficacy of the aqueous composition according to the present invention based on the front leg results of FIG. 3 and FIG. 4 and the back leg results of FIG. 7 and FIG. 8;

FIG. 10 shows a table with the daily number of domestic flies on each animal in the Treatment and Control groups from FIG. 5;

DETAILED DESCRIPTION OF THE INVENTION

Figure 1:
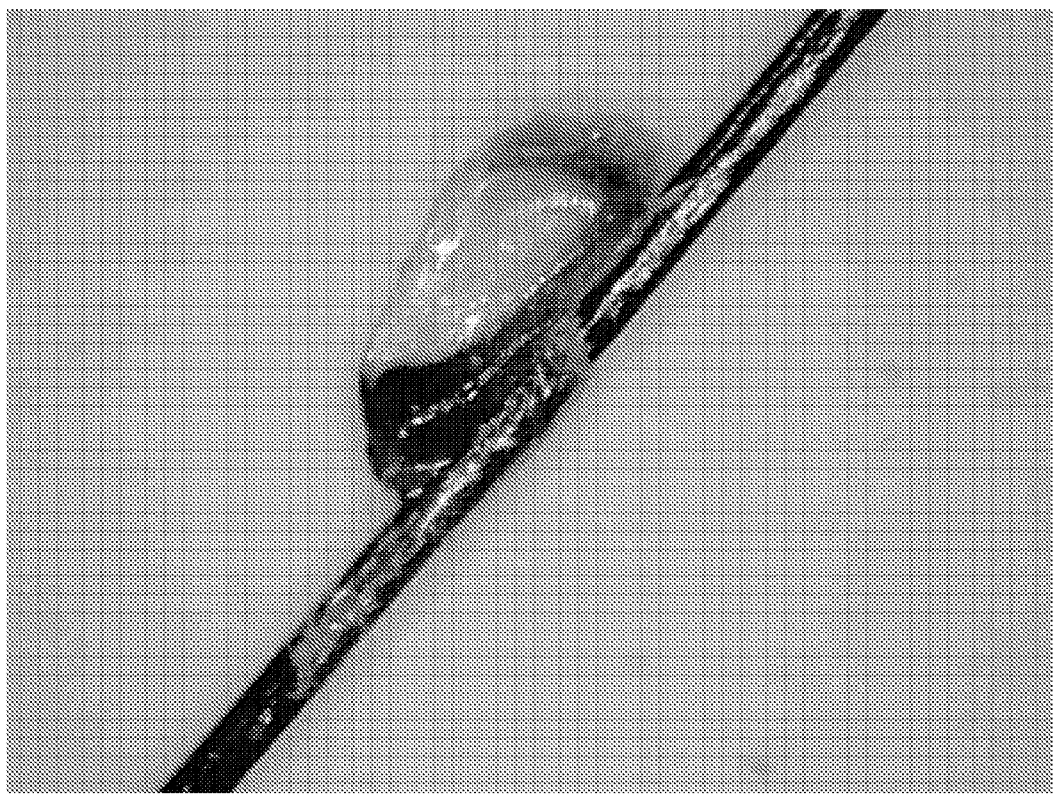
FIG. 1 shows a photo of a lice egg (nit) on hair with the glue peeling away after the application of a treatment composition in accordance with the present invention.

Exemplary embodiments of the present invention include compositions, such as aqueous compositions that may be used as pesticides, insecticides, insect repellants, insect anti-feeding compositions, cleaning solutions, glue dissolving and anti-irritation and wound and burn healing compositions for humans and animals and, more particularly, to such compositions that are effective in killing, removing and/or repelling a wide range of endoparasites, ectoparasites and insects while also being non-toxic to humans, animals, and the environment, and the methods of using such compositions for purposes, such as, but not limited to, insecticides against ectoparasites, internal parasites, bacteria, protozoa and/or fungi of humans, animals and plants, for superficial burn and wound healing, including the healing of external and internal infections and irritations that may be caused by insects, bacteria, fungi or viruses and for internal healing of the gut or other organs. For example, such compositions may be used against infective gastrointestinal protozoa, such as coccidian and cryptosporidium.

A first exemplary embodiment of the present invention is directed to an aqueous composition that includes a mixture that includes at least one amide, for example an ethanolamine, and more particularly diethanolamide, and at least one esterified fatty acid, for example a fatty acid methyl ester. The mixture of at least one amide and at least one esterified fatty acid includes mixtures such as Coconut Polydiethanolamide, Coconut Diethanolamide (Cocamide DEA), Babassu Diethanolamide, Olive Oil Fatty Acid Diethanolamide, Palm Kernel Oil Acid Diethanolamide, Palm Kernel Oil Acid Monoethanolamide, Peanut Oil Fatty Acid Monoethanolamide, Soy Oil Diethanolamide or any other mixture that includes at least one amide and at least one esterified fatty acid. For example, Cocamide DEA (coconut diethanolamide) may be a mixture of diethanolamide and the esterified fatty acids of coconut oil, and may have the following general formula:

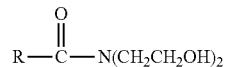

Where RCO represents the esterified fatty acids derived from the coconut oil. A variety of different Cocamide DEA formulations may be used with the present invention. For example, an exemplary formulation, referred to hereinafter as Cocamide DEA formulation A, the amide content, which may include diethanolamide, of the formulation is approximately 90% or greater of the total composition of Cocamide DEA formulation A. Furthermore, the esterified fatty acid content of Cocamide DEA formulation A may be approximately 6% or less of the total composition of Cocamide DEA formulation A. The esterified fatty acid may be a fatty acid methyl ester, such as lauric acid methyl ester, oleic acid methyl ester, palmitic acid methyl ester, myristic acid methyl ester, linoleic acid methyl ester, and stearic acid methyl ester or mixtures thereof. In addition, the free amine radical of Cocamide DEA formulation A may be approximately 5% of the total composition of Cocamide DEA formulation A.

Another exemplary formulation of Cocamide DEA, referred to hereinafter after Cocamide DEA formulation B, may also be used with the present invention. The amide content, which may include diethanolamide, of the Cocamide DEA formulation B is approximately 80% or greater of the total composition of the Cocamide DEA formulation B. Furthermore, the esterified fatty acid content of Cocamide DEA formulation B may be approximately 8-15% of the total composition of Cocamide DEA formulation B. The esterified fatty acid may be a fatty acid methyl ester, such as lauric acid methyl ester, oleic acid methyl ester, palmitic acid methyl ester, myristic acid methyl ester, linoleic acid methyl ester, and stearic acid methyl ester or mixtures thereof. In addition, the free amine radical of Cocamide DEA formulation B may be approximately 1.5% or less of the total composition of Cocamide DEA formulation B in the composition's raw form, and 0.4% or less when Cocamide DEA formulation B is included in an aqueous composition according to the present invention. The purification process of Cocamide DEA formulation B lowers the amount of free amine and also changes the fatty acid methyl ester characteristics and acid values of the formulation which provides superior insecticide strength in comparison to Cocamide DEA formulation A.

Cocamide DEA formulation B has significantly improved efficacy against insects and parasites in comparison to Cocamide DEA formulation A, and has also been shown to have efficacy in wound and minor burn healing, and have anti-parasitic and anti-bacterial properties when used as an internal composition. Compositions including Cocamide DEA formulation B are also easier to apply to the skin when compared to compositions containing Cocamide DEA formulation A, since the compositions including Cocamide DEA formulation B can be sprayed on or applied by a quick drying lotion with no greasy build-up and less of the compositions are needed for topical applications. Accordingly, compositions including Cocamide DEA formulation B have superior cosmetic acceptability and practicality of use, and since the build-up of residue from repeated applications is reduced and/or eliminated, compositions including Cocamide DEA formulation B can be used more often.

Accordingly, the aqueous composition according to the first exemplary embodiment of the invention may include 2%-50% by weight of Cocamide DEA formulation B, preferably approximately 30% by weight and 10%-90% by weight of water, preferably approximately 25% by weight.

The aqueous composition according to the first embodiment of the present invention may also include polyethylene glycol, one or more surfactants and/or detergents, one or more alcohols, one or more preservatives and one or more buffering agents. The aqueous composition may also include one or more stabilizers, emulsifiers, flow agents and/or one or more conditioning agents. The aqueous composition may also include one or more fragrances and/or one or more coloring agents.

The polyethylene glycol included in the aqueous composition may include octaethylene glycol (PEG-8), PEG-6, glyceryl ether benzoate (PEG-7), isobudecyl ether (PEG-9), glyceryl ether lactate, PEG-10, PEG-19, PEG-20 or the like.

The one or more surfactants and/or detergents that may be used in the aqueous composition may include sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate or the like.

The one or more alcohols that may be used in the aqueous composition may include ethanol, propandiol, pentylene glycol, propylene glycol, butylene glycol, benzyl alcohol, isopropanol or the like.

The buffering agent used to adjust the pH of the aqueous composition may include citric acid, lactic acid, Phosphoric Acid, Sodium Hydroxide, Triethanolamine. The buffering agent may be added to the aqueous composition as needed in order to adjust the pH to a suitable level. For example, an amount of a suitable buffering agent may be added in order to adjust the pH of the aqueous composition to 8.5 or greater or to between 7.0 and 8.0. It may be desirable to add an amount of the buffering agent to the aqueous composition so that the pH is between 7.5 and 8.0.

The preservatives used in the aqueous composition may include cocamidopropyl PG dimonium chloride phosphate, sorbic acid, methylparaben, phenoxyethanol, chlorphenesin, potassium sorbate, sodium benzoate, sodium alginate or the like.

The one or more emulsifiers, flow agents and/or stabilizers used in the aqueous composition may include PEG-120 Methyl Glucose Dioleate, Distearate-75 IPDI, xanthan gum, acadia gum, polysorbate 20, disodium cetearyl sulfosuccinamate or the like.

The conditioning agents used in the aqueous composition may include phenyl trimethicone, cetrimonium chloride, stearamidopropyl dymethylamine, hydrolyzed wheat protein, Polyquaternium-7 or the like.

The one or more fragrances used in the aqueous composition can be any fragrance whether natural or artificial, for example a citrus scent, and the one or more coloring agents can be any FDA approved food grade coloring agent.

The aqueous composition may also include acrylates copolymer in order to produce a stable gel form of the aqueous composition. Furthermore, the aqueous composition may also include dimethicone.

It is understood that an aqueous composition according to another exemplary embodiment the present invention may include at least one esterified fatty acid without the addition of one or more ethanolamides. For example, the aqueous composition may include at least one ester esterified fatty acid or a blend of esterified fatty acids, for example a blend of C8 through C18 fatty acid methyl esters. The at least one esterified fatty acid may be at least one fatty acid methyl ester, and may be any fatty acid methyl ester between C8 and C18, such as lauric acid methyl ester, caprylic acid methyl ester, capric acid methyl ester, myristic acid methyl ester, palmitic acid methyl ester, stearic acid methyl ester or unsaturated oleic acid methyl ester. In addition to or as an alternative to the at least one fatty acid methyl ester, the aqueous composition may include at least one fatty acid ethyl ester, at least one fatty acid propyl ester and/or at least one fatty acid isopropyl ester or mixtures thereof. For example, the fatty acid ethyl ester may be lauric acid ethyl ester.

The aqueous composition according to this exemplary embodiment of the present invention may include at least one emulsifier, at least one fragrance, at least one preservative and/or at least one alcohol.

The one or more alcohols that may be used in the aqueous composition may include ethanol, propandiol, pentylene glycol, propylene glycol, butylene glycol, benzyl alcohol, isopropanol or the like.

The one or more fragrances used in the aqueous composition can be any fragrance whether natural or artificial, for example a citrus or coconut scent The preservatives used in the aqueous composition may include cocamidopropyl PG dimonium chloride phosphate, sorbic acid, methylparaben, phenoxyethanol, chlorphenesin, potassium sorbate, sodium benzoate, sodium alginate or the like.

The one or more emulsifiers used in the aqueous composition may include PEG-120 Methyl Glucose Dioleate, Distearate-75 IPDI, xanthan gum, acadia gum, polysorbate 20, disodium cetearyl sulfosuccinamate or the like.

It is also understood that this exemplary embodiment of the aqueous composition may include any one of the components discussed above with respect to the first exemplary embodiment of the aqueous composition according to the present invention.

The first exemplary embodiment of the aqueous composition according to the present invention may be in the form of a shampoo composition that can be used in the treatment and/or removal of blood sucking insects, such as head lice. The components and percentages of the components by weight of the aqueous composition in the form of the shampoo composition are shown in Table 1. While Cocamide DEA formulation B is listed in Table 1 as a component of the shampoo composition, it is understood that any other suitable mixture of at least one amide, for example an ethanolamide, and more particularly diethanolamide, and at least one esterified fatty acid, for example a fatty acid methyl ester may be used in the shampoo composition according to the present invention.

TABLE 1

| Shampoo Composition | |
|---|---|
| Ingredient | % by weight |
| Water | 10-60 |
| Cocamide DEA formulation B | 5-50 |
| Polyethylene glycol | 5-50 |
| Surfactant and/or Detergent | 5-50 |
| Alcohol | 5-35 |
| Preservative | 0.1-5 |
| Buffering Agent | as needed |
| Stabilizer | 0-6 |
| Conditioning Agent | 0-6 |

In use, the shampoo composition may be applied as a shampoo on dry hair, massaged through the hair to the scalp and rinsed off after 15-20 minutes. In this manner the shampoo composition can be used as a lice killing/removing treatment and a lice egg killer/remover, and glue solvent on the hair. After the shampoo composition has been rinsed off, the insect residues may be combed out of the hair with an appropriate comb. The shampoo composition is configured to dissolve the lice egg (nit) glue produced from head lice which holds their eggs onto the hair shaft, and therefore the shampoo composition assists in the removal nits after application of the shampoo composition. FIG. 1 shows a photo of a nit on hair with the glue peeling away after the application of an aqueous composition (not necessarily the same composition listed above) in accordance with the present invention, and FIG. 1 provides an example of the manner in which the shampoo composition assists in the removal of nits. The shampoo composition may also be used as a maintenance shampoo in order to avoid reinfestation. For example, the shampoo composition may be used as a regular cosmetic shampoo at least 2 times per week in place of other cleansing shampoos by wetting the hair, lathering the shampoo composition well and rinsing the shampoo composition from the hair.

The aqueous composition may also be in the form of a spray shampoo composition, which can be used in the treatment and/or removal of blood sucking insects, such as head lice. The spray shampoo may include an additional alcohol, such as benzyl alcohol, ethanol, isopropanol, or the like, an emulsifier or flow agent such as polysorbate 20, disodium cetearyl sulfosuccinamate or the like, one or more fragrances, which can be any fragrance whether natural or artificial, and one or more coloring agents which can be any FDA approved food grade color. The components and percentages of the components by weight of the aqueous composition in the form of the spray shampoo are shown below in Table 2. While Cocamide DEA formulation B is listed in Table 2 as a component of the spray shampoo composition, it is understood that any other suitable mixture of at least one amide, for example an ethanolamide, and more particularly diethanolamide, and at least one esterified fatty acid, for example a fatty acid methyl ester may be used in the spray shampoo composition according to the present invention.

TABLE 2

| Spray Shampoo Composition | |
|---|---|
| Ingredient | % by weight |
| Water | 10-60 |
| Cocamide DEA formulation B | 5-50 |
| Polyethylene glycol | 5-50 |
| Surfactant and/or Detergent | 5-50 |
| Alcohol | 5-35 |
| Additional Alcohol | 10 |
| Emulsifier or Flow Agent | >1-5 |
| Preservative | 0.1-5 |
| Buffering Agent | as needed |
| Stabilizer | 2-6 |
| Conditioning Agent | 2-6 |
| Fragrance | >0.5 |
| Coloring Agent | >0.5 |

In use, the spray shampoo composition may be applied as a spray treatment. Enough of the spray shampoo composition is used by spraying the spray shampoo composition on the hair in order to cover all of the hair down to the scalp, e.g. 1-4 ounces. The spray shampoo composition may then be further massaged through the hair, and left to remain on the hair for 15-20 minutes and then rinsed off from the hair. The insect residues may then be combed out from the hair with an appropriate comb. The spray shampoo composition is configured to dissolve the lice egg (nit) glue produced from head lice which holds their eggs onto the hair shaft, and therefore the spray shampoo composition assists in the removal nits after application of the spray shampoo composition. FIG. 1 shows a photo of a nit on hair with the glue peeling away after the application of an aqueous composition (not necessarily the same composition listed above) in accordance with the present invention, and FIG. 1 provides an example of the manner in which the spray shampoo composition assists in the removal of nits. May repeat the spray treatment using the spray shampoo composition one week later.

The aqueous composition may also be in the form of a gel composition, which can be used in the treatment and/or removal of blood sucking insects, such as head lice. The gel composition may include acrylates copolymer, which can be used to make the gel composition into a stable gel form, Polyquaternium-7, which can be added as a hair conditioning agent, disodium cetearyl sulfosuccinamate, which can be added as a surfactant, dimethicone, which can be added as an additive to add smoothness and enhance the composition's ability to put a coating on hair, one or more fragrances and one or more coloring agents. The components and percentages of the components by weight of the aqueous composition in the form of the gel composition are shown below in Table 3.

While Cocamide DEA formulation B is listed in Table 3 as a component of the gel composition, it is understood that any other suitable mixture of at least one amide, for example an ethanolamide, and more particularly diethanolamide, and at least one esterified fatty acid, for example a fatty acid methyl ester may be used in the gel composition according to the present invention.

TABLE 3

Gel Composition

| Ingredient | % by weight |
| --- | --- |
| Water | 10-60 |
| Cocamide DEA formulation B | 5-50 |
| Polyethylene glycol | 5-50 |
| Surfactant and/or Detergent | 5-50 |
| Alcohol | 5-35 |
| Acrylates copolymer | 2-4 |
| Polyquaternium-7 | 2-6 |
| Preservative | 0.1-5 |
| Buffering Agent | as needed |
| Stabilizer | 2-6 |
| Conditioning Agent | 2-6 |
| Fragrance | >0.5 |
| Coloring Agent | >0.5 |

In use, the gel composition may be used by massaging the gel composition into the hair prior to the hair being combed to remove lice eggs. In this manner, the gel composition is allowed to remain on the hair as a combing aid until combing. The gel composition is configured to dissolve the lice egg (nit) glue produced from head lice which holds their eggs onto the hair shaft, and therefore the gel composition assists in the removal nits after application of the gel composition. FIG. 1 shows a photo of a nit on hair with the glue peeling away after the application of an aqueous composition (not necessarily the same composition listed above) in accordance with the present invention, and FIG. 1 provides an example of the manner in which the gel composition assists in the removal of nits. After combing of the hair is finished, the gel composition may then be rinsed from the hair.

The aqueous composition may also be in the form of a spray insect repellant composition and lotion composition to soothe and heal insect bites and superficial burns and skin wounds, and if so, the spray insect repellant and lotion composition may include one or more artificial or natural fragrances, such as a citrus or coconut scent. The components and percentages of the components by weight of the aqueous composition in the form of the spray repellant composition are shown below in Table 4, and components and percentages of the components by weight of the aqueous composition in the form of the lotion composition are shown below in Table 4A.

TABLE 4

Spray Repellant Composition

| Ingredient | % by weight |
| --- | --- |
| Water | 10-70 |
| Cocamide DEA formulation B | 2-25 |
| Stabilizer | 5 |
| Buffering Agent | as needed |
| Fragrance | 0.1-0.5 |

TABLE 4A

Lotion composition for aiding in the healing of scratches, cut and abrasions, bed bugs, fleas, repellence for flies, ovicidal on animal nemotodes

| Ingredient | % by weight |
| --- | --- |
| Water | 70-90 |
| Cocamide DEA formulation B | 2-20 |
| Cocamidepropyl PG Dimonium Chloride | 2 |
| Buffering Agent | 1 |
| Propanediol | 2-5 |
| Surfactant | 2-5 |

An aqueous composition according another exemplary embodiment the present invention may include one or more esterified fatty acids and water, without the addition of one or more ethanolamides. The esterified fatty acids may be one or more fatty acid methyl esters. For example, the aqueous composition may include at least one fatty acid methyl ester or a blend of fatty acid methyl esters, for example a blend of C8 through C18 fatty acid methyl esters. The fatty acid methyl ester may be any fatty acid methyl ester between C8 and C18, such as lauric acid methyl ester, caprylic acid methyl ester, capric acid methyl ester, myristic acid methyl ester, palmitic acid methyl ester, stearic acid methyl ester or unsaturated oleic acid methyl ester. The blend of C8 through C18 fatty acid methyl esters may, for example, include a blend of one or more of lauric acid methyl ester, caprylic acid methyl ester, capric acid methyl ester, myristic acid methyl ester, palmitic acid methyl ester, stearic acid methyl ester or unsaturated oleic acid methyl ester. In addition to or as an alternative to the at least one fatty acid methyl ester, the aqueous composition may include at least one fatty acid ethyl ester, at least one fatty acid propyl ester and/or at least one fatty acid isopropyl ester or mixtures thereof. For example, the fatty acid ethyl ester may be lauric acid ethyl ester.

Any combination of fatty acid methyl esters, with or without the addition of Cocamide DEA formulation B, may be used for internal or external uses for human and animals. For example, the aqueous composition may be in the form of a repellant composition, lotion composition or internal composition that may be used for insect and/or parasite repellence and/or killing. The repellant composition may be in the form of a spray repellant composition. The use of fatty acid methyl esters, or other fatty acid esters, enables the compositions to include less Cocamide DEA, for example Cocamide DEA formulation B. This provides for thinner, more sprayable and quicker drying compositions that have superior softening and conditioning effects on the skin and hair and more quickly penetrate the natural outer sheath of many insects. It also resolves the problem of oily build-up if repeated applications are needed on skin or hair. For internal use, the fatty acid methyl esters, such as lauric acid methyl esters, or particularly the fatty acid ethyl esters may be of food grade quality and nontoxic. Emulsifiers, flow and/or solvent agents, for example polysorbate 20, may be used in the compositions. The compositions can also include at least one alcohol, for example ethanol. The components and percentages of the components by weight of examples of the repellant, lotion and/or internal compositions are shown below in Tables 4B-4G.

TABLE 4B

Repellant, Lotion or Internal Composition for Endoparasites

| Ingredient | % by weight |
|---|---|
| Water | 65-95 |
| Cocamide DEA formulation B | 0.1-30 |
| Lauric Acid Ester | 0.001-15 |
| Emulsifier | 5-20 |
| Fragrance | 0.1-0.5 |
| Preservative | 0.1-5 |
| Alcohol | 0-5 |

The lauric acid ester in Table 4B may be lauric acid methyl ester or lauric acid ethyl ester or a mixture thereof.

The one or more emulsifiers, flow agents and/or stabilizers used in the aqueous composition described in Table 4B and any of the Tables below may include PEG-120 Methyl Glucose Dioleate, Distearate-75 IPDI, xanthan gum, acadia gum, polysorbate 20, disodium cetearyl sulfosuccinamate or the like.

The one or more alcohols that may be used in the aqueous composition described in Table 4B and any of the Tables below may include ethanol, propandiol, pentylene glycol, propylene glycol, butylene glycol, benzyl alcohol, isopropanol or the like.

The one or more fragrances used in the aqueous composition described in Table 4B and any of the Tables below can be any fragrance whether natural or artificial, for example a citrus scent The preservatives used in the aqueous composition described in Table 4B and any of the Tables below may include cocamidopropyl PG dimonium chloride phosphate, sorbic acid, methylparaben, phenoxyethanol, chlorphenesin, potassium sorbate, sodium benzoate, sodium alginate or the like.

The formulation identified in Table 4B may be used for any and/or all of the purposes discussed above and/or mentioned below. For example, the formulation is particularly effective against insects, such as mosquitoes, bedbugs, ticks, flies, spiders. Furthermore, the formulation may be used for internal purposes in amounts between 0.1 and 20 mL.

TABLE 4C

Spray repellent or Internal Composition

| Ingredient | % by weight |
|---|---|
| Water | 75-95 |
| Lauric Acid Ester | 0.001-15 |
| Emulsifier | 5-20 |
| Fragrance | 0.1-0.5 |
| Preservative | 0.1-5 |
| Alcohol | 0-5 |

The lauric acid ester in Table 4C may be lauric acid methyl ester or lauric acid ethyl ester or a mixture thereof.

TABLE 4D

Repellant, Lotion or Internal Composition

| Ingredient | % by weight |
|---|---|
| Water | 75-95 |
| Lauric Acid Ester | 0.001-15 |
| Emulsifier | 5-20 |
| Alcohol | 1-5 |

The lauric acid ester in Table 4D may be lauric acid methyl ester or lauric acid ethyl ester or a mixture thereof.

TABLE 4E

Repellant, Lotion or Internal Composition

| Ingredient | % by weight |
|---|---|
| Water | 75-95 |
| Blend of C8 to C18 Fatty Acid Methyl Esters | 0.001-15 |
| Emulsifier | 5-20 |
| Alcohol | 0-5 |

The blend of C8 through C18 fatty acid methyl esters may include a blend of one or more of lauric acid methyl ester, caprylic acid methyl ester, capric acid methyl ester, myristic acid methyl ester, palmitic acid methyl ester, stearic acid methyl ester or unsaturated oleic acid methyl ester.

TABLE 4F

Repellant, Lotion or Internal Composition

| Ingredient | % by weight |
|---|---|
| Water | 75-95 |
| Caprylic Acid Methyl Ester | 0.001-15 |
| Emulsifier | 5-20 |
| Alcohol | 0-5 |

TABLE 4G

Repellant, Lotion or Internal Composition

| Ingredient | % by weight |
|---|---|
| Water | 75-95 |
| Capric Acid Methyl Ester | 0.001-15 |
| Emulsifier | 5-20 |
| Alcohol | 0-5 |

In use, any of the repellant, lotion and/or internal compositions may be used for pesticides, insecticides, insect repellants, insect anti-feeding compounds, cleaning solutions, glue dissolving solutions and anti-irritation and wound healing compositions for humans and animals and, more particularly, may be used for killing, removing and/or repelling a wide range of endoparasites, ectoparasites and insects. The repellant, lotion and/or internal composition may also be used for purposes, such as, but not limited to, insecticides against ectoparasites, internal parasites, bacteria, protozoa and/or fungi of humans, animals and plants, for superficial burn and wound healing, including the healing of external irritations that may be caused by insects, bacteria, fungi or viruses and for internal healing of the gut or other organs and infective gastrointestinal protozoa including coccidian and cryptosporidium. Accordingly, through the use of esterified medium chain fatty acids, the repellant, lotion and/or internal compositions have activity against a wide range of organisms and biological systems, including arthropods (mites and insects), protozoal pathogens, bacteria and cells involved in wound healing and internal bacterial infections.

Example I

Materials and Methods

The collecting technicians washed their hands with antibacterial soap and rinsed in clean tap water, followed by a rinse in 70% isopropanol to remove any possible contaminants. Using a lighted circular 6× magnifying lamp, the technicians collected lice from the heads of infested individuals. Lice of all stages were distributed among 4 prepared Petri dishes (15×60 mm). Each prepared Petri dish contained two 100% cotton cloth disk. The 100% cotton cloth disk was obtained from cotton kitchen towels that had been washed with a small quantity of non-medicated anionic shampoo, thoroughly rinsed and dried. Five centimeter diameter disks were cut from the prepared towels to form the 100% cotton cloth disks and to simulate hair. The cotton cloth disks in three Petri dishes were saturated in 1 mL of a treatment composition, and the cotton cloth disk in the fourth Petri dish was saturated in 1 distilled water, all cotton cloth disks were dampened with distilled water to prevent dehydration. The treatment composition is shown below in Table 5. Observation began when lice were placed on treatment, and observed at five minute intervals. Lice remained in treatment for 20 minutes and at that point the disk with lice was removed and transferred and placed on top of stretched panty hose over a beaker devised for the purpose of rinsing. The lice and disk were rinsed with 100 mL of distilled water. Observations were made as follows:

Behavior: Unsteady gait (drunkenness), stumbling, disorientation, convulsions, tremors, hyper-excitability, and response to light, warmth, and carbon dioxide.

Physical Signs: Bloating, dehydration, extrusion of gonads in males, excretion of blood meal, signs of peripheral nerve discharges, CNS toxicity, etc.

Moribund: Inability to walk, turn over when placed on their back, and have only occasional twitch or tremor of legs or antennae. Note: Lice never resurrect or recover from this stage.

Death: When all movement of limbs, antennae, and peristalsis of the gut cease.

TABLE 5

Treatment composition

| Ingredient | % by weight |
| --- | --- |
| Water | 25 |
| Cocamide DEA formulation B | 30 |
| Polyethylene glycol | 30 |
| Sodium Methyl Cocoyl Taurate | 6 |
| Propanediol | 5 |
| Sodium Laureth Sulfate | 2 |
| Cocamidopropyl PG Dimonium Chloride Phosphate | 1 |
| Citric Acid | 1 |

Results

TABLE 5A

Number of alive lice

| Dish No. | Number of Lice Alive at T = 0 min | Number of Lice Alive at T = 5 min | Number of Lice Alive at T = 10 min | Number of Lice Alive at T = 15 min | Number of Lice Alive at T = 360 min |
| --- | --- | --- | --- | --- | --- |
| 1 | 20 | 4 | 0 | 0 | 0 |
| 2 | 20 | 3 | 0 | 0 | 0 |
| 3 | 20 | 3 | 1 | 0 | 0 |
| Control | 31 | 31 | 31 | 31 | 31 |

Example II

Materials and Methods

The collecting technicians washed their hands with antibacterial soap and rinsed in clean tap water, followed by a rinse in 70% isopropanol to remove any possible contaminants. Using a lighted circular 6× magnifying lamp, the technicians collected lice from the heads of infested individuals. A total of 46 lice of all stages were distributed among 4 prepared Petri dishes (15×60 mm). Each prepared Petri dish contained a 100% cotton cloth disk. The 100% cotton cloth disk was obtained from cotton kitchen towels that had been washed with a small quantity of non-medicated anionic shampoo, thoroughly rinsed and dried. Five centimeter diameter disks were cut from the prepared towels to form the 100% cotton cloth disks and to simulate hair. The cotton cloth disk in one Petri dish was saturated in 2 mL of a treatment composition, and the cotton cloth disks in the other three Petri dishes were saturated in 1 mL of the treatment composition, all cotton cloth disks were dampened with distilled water to prevent dehydration. The treatment composition is shown below in Table 6. Observation began when lice were placed on treatment. Lice remained in treatment for 20 minutes and at that point the disk with lice was removed and transferred and placed on top of stretched panty hose over a beaker devised for the purpose of rinsing. The lice and disk were rinsed with 100 mL of distilled water. Observations were made as follows:

Behavior: Unsteady gait (drunkenness), stumbling, disorientation, convulsions, tremors, hyper-excitability, and response to light, warmth, and carbon dioxide.

Physical Signs: Bloating, dehydration, extrusion of gonads in males, excretion of blood meal, signs of peripheral nerve discharges, CNS toxicity, etc.

Moribund: Inability to walk, turn over when placed on their back, and have only occasional twitch or tremor of legs or antennae. Note: Lice never resurrect or recover from this stage.

Death: When all movement of limbs, antennae, and peristalsis of the gut cease.

TABLE 6

Treatment composition

| Ingredient | % by weight |
| --- | --- |
| Water | 25 |
| Cocamide DEA formulation B | 30 |
| Polyethylene glycol | 30 |
| Sodium Methyl Cocoyl Taurate | 6 |
| Propanediol | 5 |
| Sodium Laureth Sulfate | 2 |
| Cocamidopropyl PG Dimonium Chloride Phosphate | 1 |
| Citric Acid | 1 |

Results

Death was instantaneous for 91% (42 out of 46 lice) upon contact with the treatment. For these lice, peristalsis of the gut ceased immediately and there was no movement, twitching or any other activity to be observed. Within 5 minutes of exposure 96% (44 out of 46) were dead and within 10 minutes all (100%) of the lice were dead.

Example III

Material and Methods

A study was conducted to test the efficacy against head lice (Pediculosis captitis) and nits using one fifteen minute treatment of the treatment composition show in Table 7. Subjects for the study were selected based on the presence of an active infestation of head lice, with at least three live lice and viable appearing eggs. Subjects did not use any other pediculicides or medicated hair grooming products during the duration of the study, and were otherwise healthy, non-febrile and not suffering from an infection likely to require antibiotic therapy during the study period. The total duration of the study was 8 days, with the treatment composition being applied on Day 1 and a one-week follow up visit on Day 8. The treatment composition was applied in one fifteen minute application to the dry hair and scalp of the test subjects, re-massaged through the hair, rinsed with water, combed thoroughly and naturally dried. Sixty subjects from fifteen households were included in the study with the following breakdown of ages:

- 2-6 years of age . . . 14 test subjects
- 7-17 years of age . . . 38 test subjects
- 18-70 years of age . . . 8 test subjects After treatment on Day 1 the test subjects were observed for the presence or absence of live lice. On Day 8 visual examination of the test subjects was conducted using a lighted 5× magnifier for the stage of nymphs or adults.

TABLE 7

Treatment composition

| Ingredient | % by weight |
| --- | --- |
| Water | 25 |
| Cocamide DEA formulation B | 30 |
| Polyethylene glycol | 30 |
| Sodium Methyl Cocoyl Taurate | 6 |
| Propanediol | 5 |
| Sodium Laureth Sulfate | 2 |
| Cocamidopropyl PG Dimonium Chloride Phosphate | 1 |
| Citric Acid | 1 |

Results

All lice were dead on Day 1 of the treatment, nits were loosened and many nits fell out even without combing. The treatment composition was 100% effective on Day 1.

Example IV

Material and Methods

A study was conducted to test the efficacy against head lice (Pediculosis captitis) and nits using one fifteen minute treatment of the treatment composition show in Table 8. Subjects for the study were selected based on the presence of an active infestation of head lice, with at least five live lice present. Subjects did not use any other pediculicides or medicated hair grooming products during the duration of the study, and were otherwise healthy, non-febrile and not suffering from an infection likely to require antibiotic therapy during the study period. The total duration of the study was 7 days, with the treatment composition being applied on Day 1, combing and inspection on Day 2 and a follow up combing and inspection on Day 7. The treatment composition was applied in one fifteen minute application to the dry hair and scalp of the test subjects, re-massaged through the hair, rinsed with water, combed and dried with an electric hairdryer. Sixteen test subjects were treated on Day 1 followed by combing and inspection on Day 2, and another combing on Day 7. Eleven other test subjects were treated and combed with a nit comb immediately after the treatment composition had been washed out of the subjects' hair. The eleven test subjects were combed with separate nit combs until the subjects' hair was clear of all lice and nits. The comb was placed in a bag and taken to a laboratory for further inspection.

TABLE 8

Treatment composition

| Ingredient | % by weight |
| --- | --- |
| Water | 25 |
| Cocamide DEA formulation B | 30 |
| Polyethylene glycol | 30 |
| Sodium Methyl Cocoyl Taurate | 6 |
| Propanediol | 5 |
| Sodium Laureth Sulfate | 2 |
| Cocamidopropyl PG Dimonium Chloride Phosphate | 1 |
| Citric Acid | 1 |

Results

Of the sixteen test subjects, all of the test subjects were lice free on Day 2, and on the combing on Day 7 five of the test subjects had one or more adult louse present indicative of a recent re-infestation. Of the nit combs obtained from the other eleven test subjects four of the nit combs showed no evidence of lice or nits in any stage, and seven of the nit combs showed dead lice or various developmental stages and nits.

Example V

Methods

Head lice were collected by human volunteers and placed in vials containing either the treatment composition listed in Table 9 or water as a control. Five vials containing the treatment composition were provided with ten nits each and two vials containing the water control were provided with five nits each. The ovicidal activity in each of the vials was observed for a ten day period. The weather, temperature and relative humidity was recorded for each of the ten days, and show in Table 10 below.

TABLE 9

Treatment composition

| Ingredient | % by weight |
| --- | --- |
| Water | 25 |
| Cocamide DEA formulation B | 30 |
| Polyethylene glycol | 30 |
| Sodium Methyl Cocoyl Taurate | 6 |
| Propanediol | 5 |
| Sodium Laureth Sulfate | 2 |
| Cocamidopropyl PG Dimonium Chloride Phosphate | 1 |
| Citric Acid | 1 |

TABLE 10

Weather conditions during test period

| Day | Weather | Temperature (° F.) | Relative Humidity (%) |
| --- | --- | --- | --- |
| Day 1 | Fair | 86 | 70 |
| Day 2 - 8:20 AM | Fair | 84.2 | 70 |
| Day 2 - 4:20 PM | Fair | 86 | 70 |
| Day 3 - 8:20 AM | Fair | 82.4 | 69 |
| Day 3 - 4:20 PM | Fair | 86 | 70 |
| Day 4 - 8:20 AM | Fair | 78.8 | 69 |
| Day 4 - 8:20 PM | Fair | 91.4 | 70 |

TABLE 10-continued

Weather conditions during test period

| Day | Weather | Temperature (° F.) | Relative Humidity (%) |
|---|---|---|---|
| Day 5 - 8:30 AM | Fair | 82.4 | 69 |
| Day 5 - 4:20 PM | Fair | 86 | 70 |
| Day 6 - 9:00 AM | Fair | 84.2 | 70 |
| Day 6 - 4:30 PM | Fair | 86 | 70 |
| Day 7 - 8:00 AM | Rain | 82.4 | 68 |
| Day 7 - 4:00 PM | Rain | 84.3 | 70 |
| Day 8 - 9:00 AM | Rain | 82.4 | 69 |
| Day 8 - 4:00 PM | Rain | 86 | 70 |
| Day 9 - 8:00 AM | Fair | 80.6 | 69 |
| Day 9 - 4:00 PM | Fair | 84.2 | 70 |
| Day 10 - 9:00AM | Fair | 84.2 | 68 |

Results

TABLE 11

Results showing ovicidal activity

| Vial No. | | # of Nits in Vial | # of Nits Hatched |
|---|---|---|---|
| 1 | Treatment Composition | 10 | 0 |
| 2 | Treatment Composition | 10 | 0 |
| 3 | Treatment Composition | 10 | 2 |
| 4 | Treatment Composition | 10 | 0 |
| 5 | Treatment Composition | 10 | 0 |
| 1-C | Water | 5 | 4 |
| 2-C | Water | 5 | 3 |

Example VI

Glue Dissolving Properties of Treatment Composition

Lice eggs remaining on hairs due to the natural nit glue produced by the female louse were dipped in the composition shown in Table 9 and observed and photographed within 30 days. Glue was observed dissolving and peeling off the hair shaft as shown in FIG. 1.

Example VII

An aqueous solution containing Cocamide DEA formulation B aids in the healing process of wounds and reducing scarring. An aqueous formulation containing 7% Cocamide DEA formulation B as shown in Table 4, i.e. a formulation containing approximately 10-70% water, 7% Cocamide DEA formulation B, 5% of a stabilizer, a buffering agent and 0.1-0.5 of a fragrance was applied several times in one day to deep cat scratches on human skin. The solution was found to be soothing, and healing took place within 48 hours with no scarring. The formulation has good analgesic properties and promotes the healing process. The formulation eliminated the pain of deep cat scratches and accelerated healing without scaring on a human subject. Similar results were obtained on volunteers when a 5-10% aqueous solution was applied to various skin cuts and abrasions.

The formulation is also shown to be bacteriostatic for certain common skin surface bacteria. The formulation has also been shown to help reduce the itching and speed up the healing process associated with insect bites.

Figure 14:
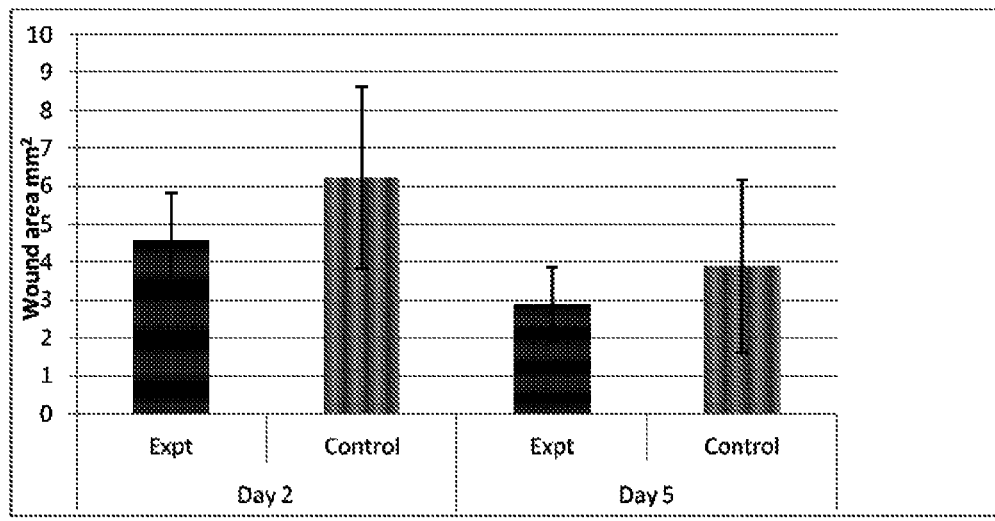
FIG. 14 shows a chart of wound size at day two and day five for wounds that were treated with a treatment formulation according to the present invention and wounds that received no treatment at all.

Furthermore, a trial of the formulation on puncture wounds gave a significant difference in the healing process between wounds left untreated and those treated with the formulation. Pathological sections of the wounds showed the re-introduction of hair follicles in treated sections, but not in the control sections. FIG. 14 shows a chart showing wound size of treated and untreated wounds at days two and five. In FIG. 14, "Expt" wounds were treated with a diluted formulation, while "Control" wounds received no treatment at all. Accordingly, the formulation has major medical potentials for use in both over the counter products for cuts and grazes, and in more serious medical conditions such as burns, ulcers, bed sores and many post surgical procedures where promotion of healing would be useful.

Example VIII

TABLE 12

Treatment Composition

| Ingredient | % by weight |
|---|---|
| Water | 80 |
| Cocamide DEA formulation B | 2 |
| Propanediol | 2-5 |
| Surfactant | 2-5 |
| Cocamidopropyl PG Dimonium Chloride Phosphate | 2 |
| Citric Acid | 1 |

Bed Bugs: Several concentrations of the treatment composition listed in Table 12 were prepared in dilutions of 2%-10% in water base. A quick knock down effect when lower concentrations of the treatment composition listed in Table 12 were used (2-5% and high kill rates with higher concentration ranges of the treatment composition shown in Table 12 (5-10%).

Groups of Bed Bugs were dipped in the treatment composition shown in Table 12, while several others had composition lightly painted on body with a brush. All bed bugs were quickly knocked down and became motionless upon application. All bed bugs dipped in composition died within minutes. Bed bugs lightly brushed with composition slowly recovered after one hour.

Water control showed Beg bugs remained alive with little or no knock down effect.

Example IX

The treatment composition listed in Table 12 was rubbed gently on skin. Tsetse flies avoided contact with skin and would not feed, the tsetse flies only initiated feeding when they could avoid walking on a treated surface. When the treatment composition came in contact with the feet of the tsetse fly, they died. When fed through a treated membrane the tsetse flies quickly died.

Example X

Figure 2:
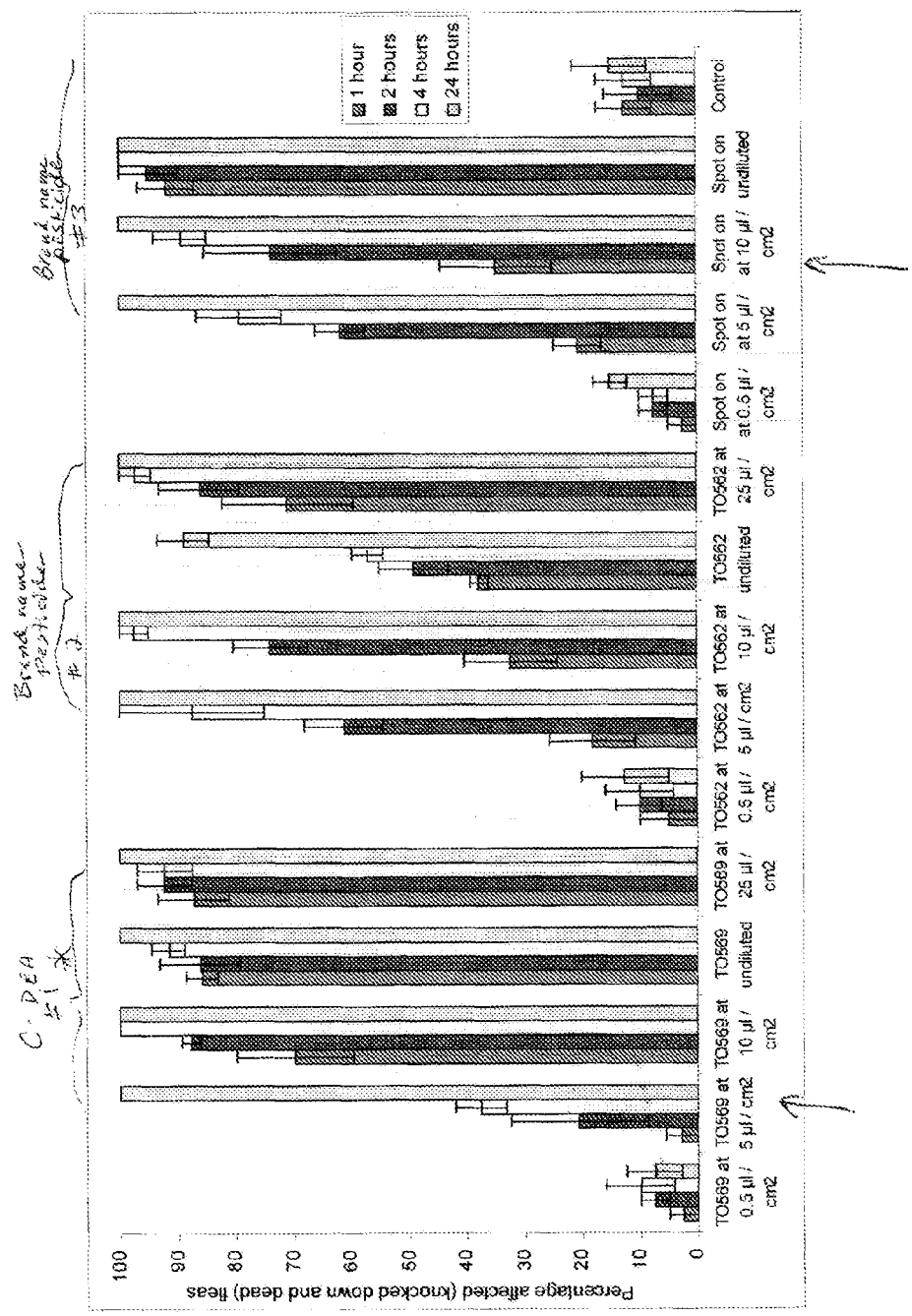
FIG. 2 shows a comparison of repellence efficacy of an aqueous composition according to the present invention and two other pesticide spot-on repellants.
Figure 3:
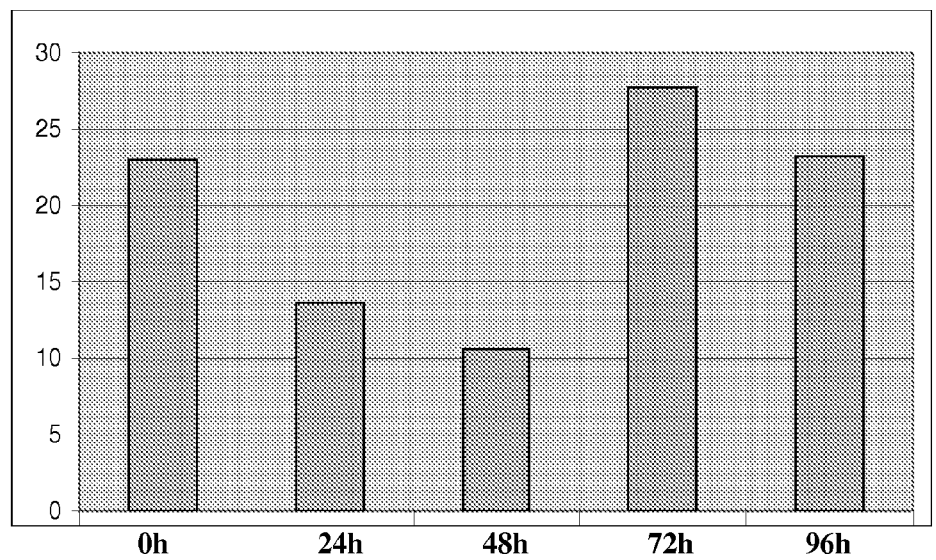
FIG. 3 shows a chart of the number of domestic flies on the front legs of dairy cows that have had an aqueous composition according to the present invention applied to them.
Figure 4:
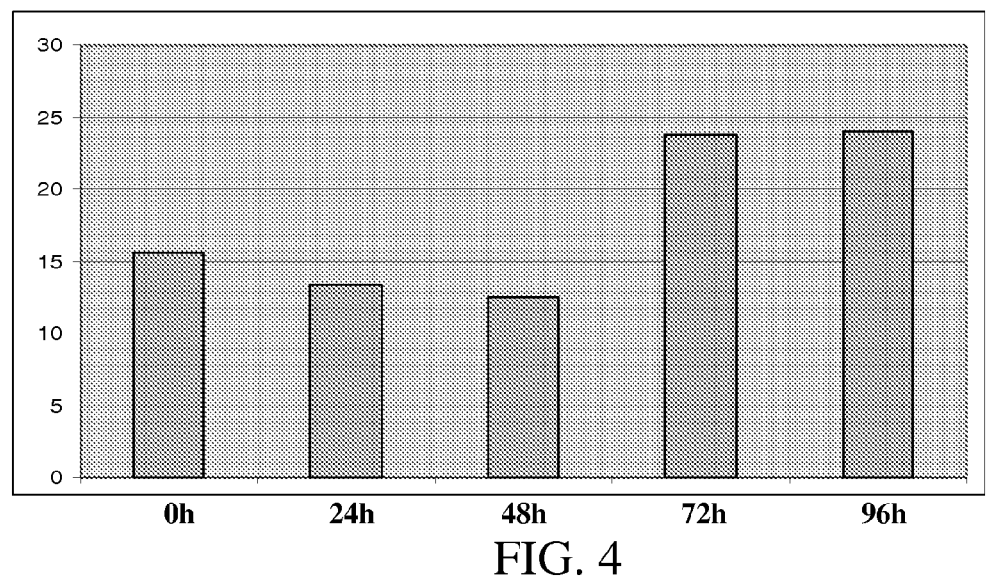
FIG. 4 shows a chart of the number of domestic flies on the front legs of dairy cows that have not have not had an aqueous composition according to the present invention applied to them, i.e. a control for the chart shown in FIG. 3.
Figure 5:
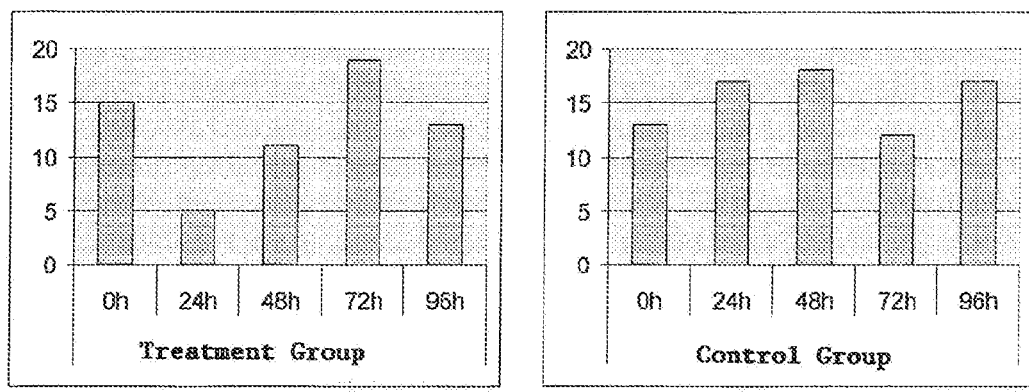
FIG. 5 shows a pair of charts of the number of domestic flies on the front legs of dairy cows that have had an aqueous composition (Treatment Group) according to the present invention applied to them, and the front legs of dairy cows that have not had an aqueous composition (Control Group) according to the present invention applied to them.
Figure 7:
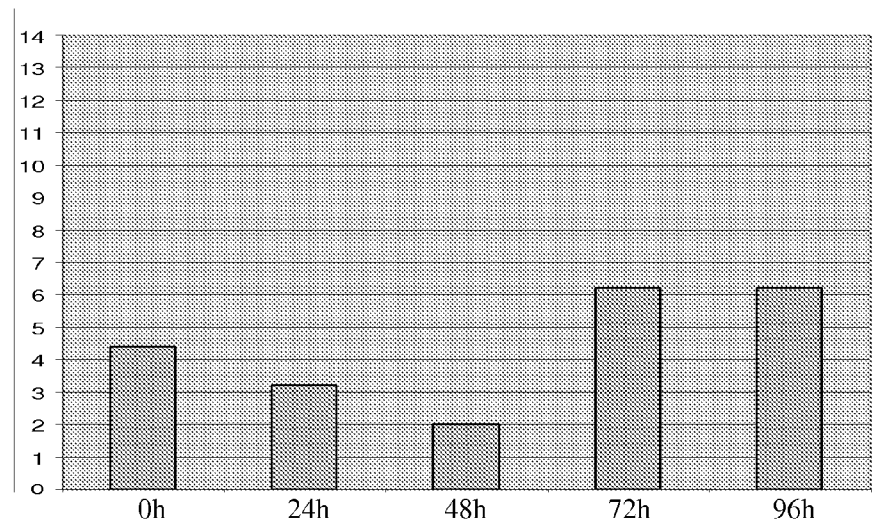
FIG. 7 shows a chart of the number of domestic flies on the back legs of dairy cows that have had an aqueous composition according to the present invention applied to them.
Figure 8:
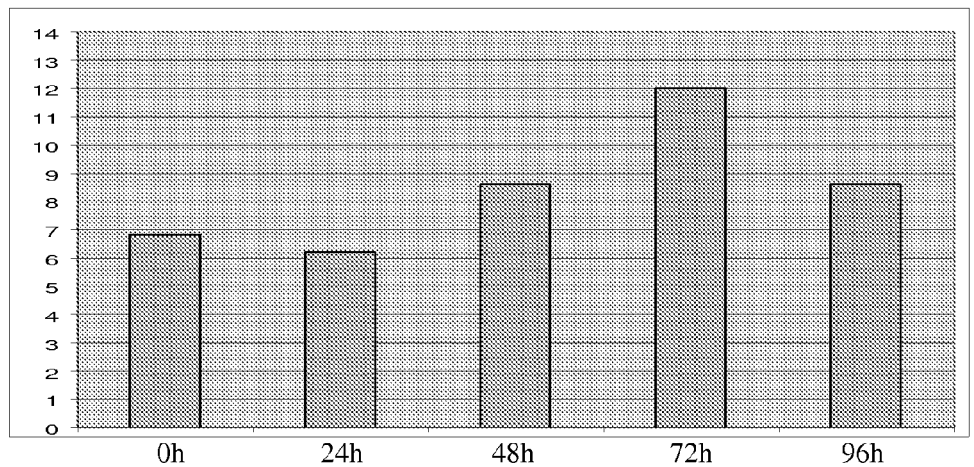
FIG. 8 shows a chart of the number of domestic flies on the back legs of dairy cows that have not have not had an aqueous composition according to the present invention applied to them, i.e. a control for the chart shown in FIG. 7.
Figure 11:
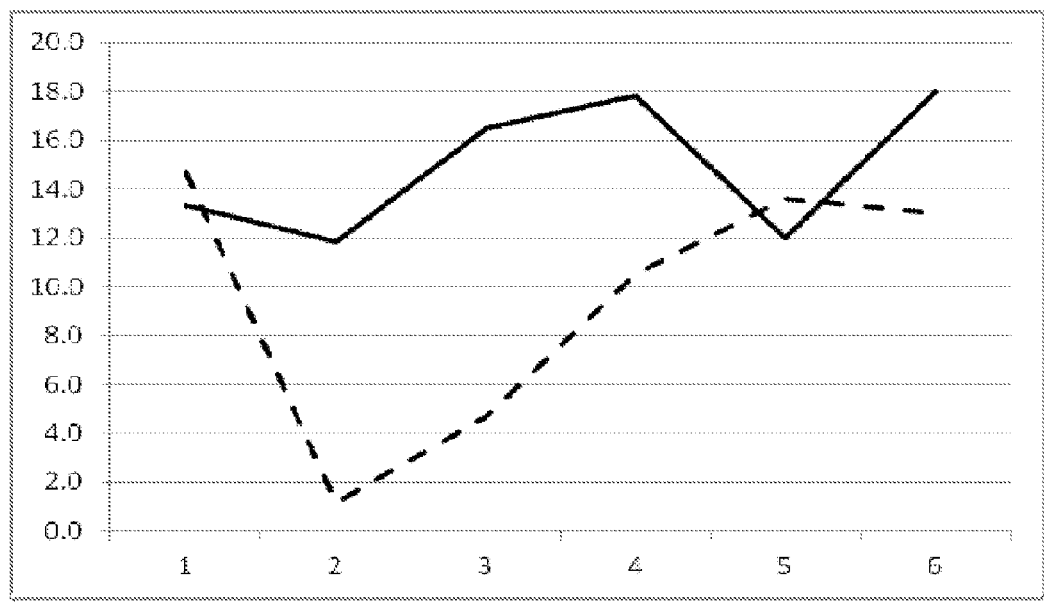
FIG. 11 shows a graph of the results shown in FIG. 5.

Spot on Treatment for fleas on animals: Cocamide DEA formulation B (in an aqueous carrier was tested in various dilutions (0.05%-50%) for repellence efficacy against 2 leading pesticide spot-on repellents. After 24 hours the formulation worked as well or better than both pesticides as shown in FIG. 2. The first group on the graph of FIG. 2 was an aqueous solution of Cocamide DEA using 5 strengths noted on the graph shown in FIG. 2.

Example XI

Repellence again domestic flies on front legs and back legs of Dairy Cows. The treatment composition listed in Table 12 was applied to the front and back legs of dairy cows. FIGS. 3-11 shows that repellence lasts up to 2 days when compared to the control.

Repellence against horn flies (*Haematobia irritans*) in Brazil showed protection for up to 4 days. Repellence against ticks in a field trial showed no bites on a leg with the treatment composition from Table 11 when compared to an untreated leg.

Example XII

Figures 12, 13:
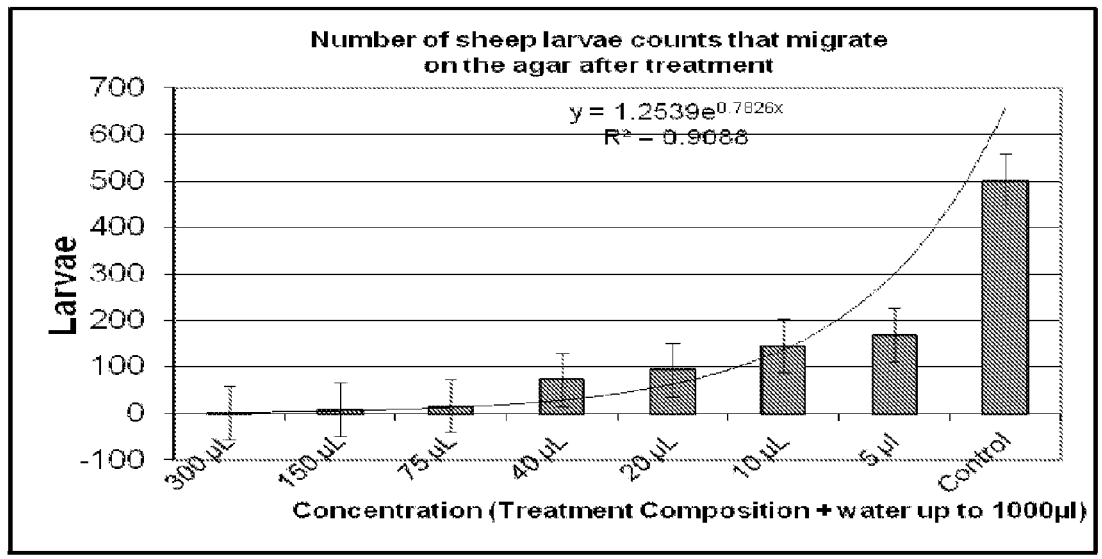
FIG. 12 shows a chart with larvae migration test results for nematode larvae derived from sheep that were placed in increasing concentrations of an aqueous composition according to the present invention.
FIG. 13 shows a chart with larvae migration test results for nematode larvae derived from sheep that were placed in increasing concentrations of an aqueous composition according to the present invention.

In a larvae migration experiment, nematode (*haemonchus*) larvae derived from sheep were placed in increasing concentrations of the treatment composition of Table 12. Larvae were incubated for 6 hours in three replicates and transferred to a 1.4% agar solution for a second incubation of 18 hours. The final counts are based on the L3 that have migrated out of the agar. Doses were done in triplicates. The results of the larvae migration test are shown in FIGS. 12 and 13, and show the average, standard deviation and dose dependent effect.

Example XIII

Figure 15:
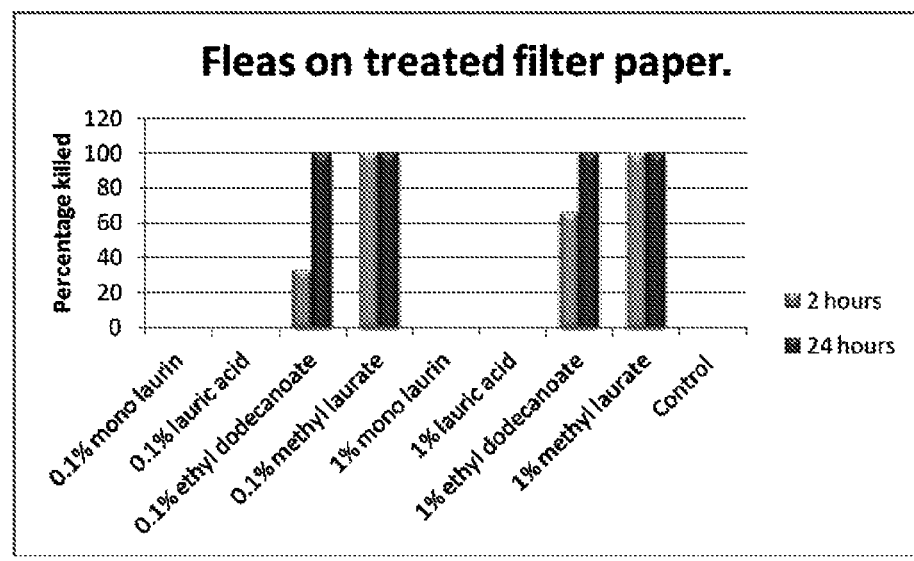
FIG. 15 shows a chart with the percentage of fleas killed two and 24 hours after exposure of the fleas to filter paper treated with the compounds listed in the chart.

FIG. 15 shows the results from a test comparing the efficacy of fatty acids to fatty acid methyl and fatty acid ethyl esters on fleas. The fatty acids used in the test were mono laurin and lauric acid, while the fatty acid esters used in the test were methyl laurate, i.e. lauric acid methyl ester and ethyl dodecanoate, i.e. lauric acid ethyl ester. Each of these compounds were dissolved in ethanol in concentrations of 0.1% and 1%, and then 200 µL (micro liters) of each solution was placed on glass filter paper (15×150 mm). After the ethanol had evaporated a paper for each concentration of each compound was put into a test tube, and 12 fleas were added per test tube and the top of the test tube was covered. Whether the fleas were alive or dead at was measured after 2 and twenty-four hours. As shown in FIG. 15 both concentrations, i.e. 0.1% and 1% of lauric acid methyl ester and lauric acid ethyl ester showed 100% mortality of the fleas after twenty-four hours. The results indicate that fatty acid methyl and ethyl esters work far better than plain fatty acids. Further results are shown below in Table 13.

TABLE 13

Results for flea contact test using impregnated glass paper. The percentage killed is after 24 hours.

| Composition | 2 Hours | | 24 hours | | % Killed |
|---|---|---|---|---|---|
| | Alive | Dead | Alive | Dead | |
| ISDE - 1% (benign base) | 12 | 0 | 12 | 0 | 0 |
| NG1:3 + 1% ISDE | 12 | 0 | 9 | 3 | 25 |
| NG 1:3 + 1% C12 | 12 | 0 | 4 | 8 | 67 |
| NG 1:3 + 1% C12 + 1% ISDE | 11 | 1 | 0 | 12 | 100 |
| NG 1:3 + 1% C10 | 3 | 9 | 1 | 11 | 92 |
| NG 1:3 + 1% C10 + 1% ISDE | 12 | 0 | 0 | 12 | 100 |
| NG 1:3 + 1% C8 | 11 | 1 | 11 | 1 | 8 |
| NG 1:3 + 1% C8 + 1% ISDE | 12 | 0 | 12 | 0 | 0 |
| Vial C (New CDEA/water/Polysorbate 20) | 1 | 11 | 0 | 12 | 100 |
| Vial E (C8-C18/water/Polysorbate) | 2 | 10 | 0 | 12 | 100 |
| Vial B (Original CDEA/water/polysorbate) | 12 | 0 | 11 | 1 | 8 |
| Vial D (C12/water/polysorbate) | 2 | 10 | 0 | 12 | 100 |
| Vial G (C-8/water/polysorbate) | 12 | 0 | 10 | 2 | 17 |
| Vial F (C-18/water/polysorbate) | 12 | 0 | 10 | 2 | 17 |
| Control (water/polysorbate) | 12 | 0 | 12 | 0 | 0 |
| Water | 12 | 0 | 12 | 0 | 0 |

The test samples named in Table 13 are composed as follows:
ISDE is isosorbide dimethyl ether;
NG 1:3 is a 7.5% solution of Cocamide DEA formulation B;
C8 represents caprylic acid methyl ester;
C10 represents capric acid methyl ester;
C12 represents lauric acid methyl ester;
C14 represents myristic acid methyl ester;
C16 represents palmitic acid methyl ester;
C18 represents stearic acid methyl ester or unsaturated oleic acid methyl ester;
C8-C18 represents a blend of the fatty acid methyl esters listed above;
Vial B—7.5% Cocamide DEA formulation A, 90.5% water and 2% Polysorbate 20;
Vial C—7.5% Cocamide DEA formulation B, 3% lauric acid methyl ester, 2% Polysorbate 20 and water to 100%;
Vial D—5% lauric acid methyl ester, 8%, Polysorbate 20 and water to 100%;
Vial E—5% C8-C18, 8% Polysorbate 20 and water to 100%;
Vial F—5% C18, 8% Polysorbate 20 and water to 100%;
Vial G—5% C8, 8% Polysorbate 20 and water to 100%;
Control—8% Polysorbate 20 and water to 100%.
Further results are shown below in Table 14, regarding the efficacy of various fatty acid methyl and ester esters against fleas (*ctenocephalides felis*).

TABLE 14

Comparison of efficacy of various fatty acid methyl and ethyl esters in water or acetone against *ctenocephalides felis*

| Ctenocephalides felis on glass paper | | 2 hours | | 5 Hours | | 20 hours | |
|---|---|---|---|---|---|---|---|
| | | Alive | Dead | Alive | Dead | Alive | Dead |
| Methyl octanoate - 1% | Water | 5 | 0 | 5 | 0 | 5 | 0 |
| Methyl nonanoate - 1% | Water | 14 | 0 | 14 | 0 | 14 | 0 |
| Methyl decanoate - 1% | Water | 19 | 0 | 19 | 0 | 19 | 0 |
| Methyl octanoate - 0.1% | Water | 10 | 0 | 10 | 0 | 10 | 0 |
| Methyl nonanoate - 0.1% | Water | 12 | 0 | 12 | 0 | 12 | 0 |
| Methyl decanoate - 0.1% | Water | 11 | 0 | 11 | 0 | 11 | 0 |
| Methyl octanoate - 1% | Acetone | 8 | 0 | 8 | 0 | 8 | 0 |
| Methyl nonanoate - 1% | Acetone | 9 | 0 | 9 | 0 | 9 | 0 |
| Methyl decanoate - 1% | Acetone | 14 | 0 | 14 | 0 | 14 | 0 |
| Methyl octanoate - 0.1% | Acetone | 16 | 0 | 16 | 0 | 16 | 0 |
| Methyl nonanoate - 0.1% | Acetone | 14 | 0 | 14 | 0 | 14 | 0 |
| Methyl decanoate - 0.1% | Acetone | 12 | 0 | 12 | 0 | 12 | 0 |
| Methyl laurate - 1% | Water | 11 | 0 | 11 | 0 | 11 | 0 |
| Methyl laurate - 0.1% | Water | 15 | 0 | 15 | 0 | 15 | 0 |
| Methyl laurate - 1% | Acetone | 0 | 13 | 0 | 13 | 0 | 13 |
| Methyl laurate - 0.1% | Acetone | 15 | 0 | 15 | 0 | 15 | 0 |
| Water control | | 10 | 0 | 10 | 0 | 10 | 0 |
| Acetone control | | 10 | 0 | 10 | 0 | 10 | 0 |

Example XIV

Figure 16:
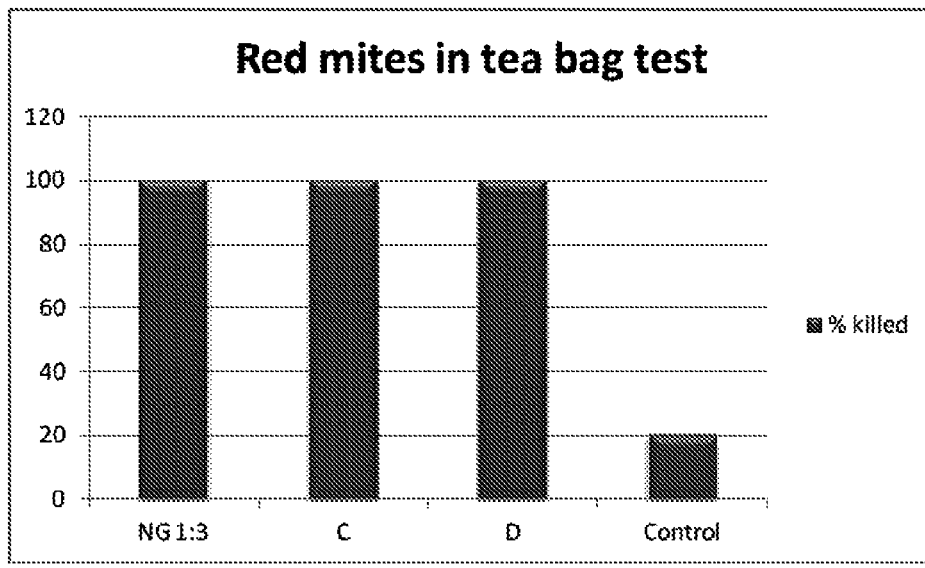
FIG. 16 shows a chart with the results from a test regarding the efficacy of solutions containing Cocamide DEA formulation B and/or fatty acid esters against red mites.
Figure 17:
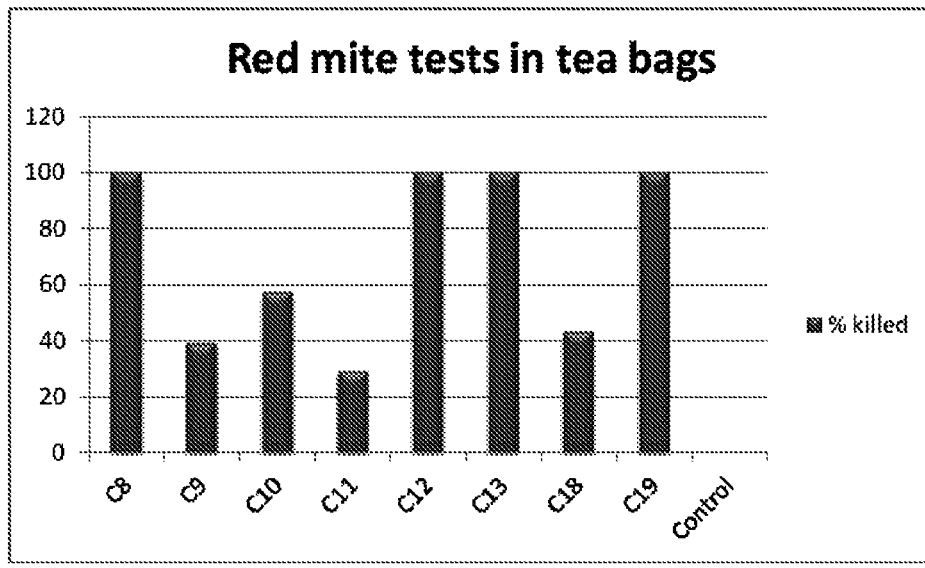
FIG. 17 shows a chart with the results from a test regarding the efficacy of solutions containing Cocamide DEA formulation B and/or fatty acid esters against red mites.
Figure 18:
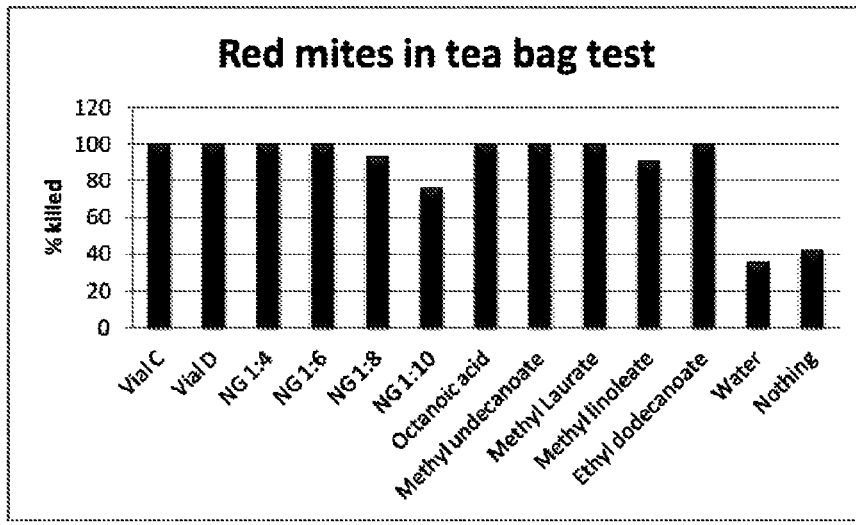
FIG. 18 shows a chart with the results from a test regarding the efficacy of solutions containing Cocamide DEA formulation B and/or fatty acid esters against red mites.

FIGS. 16-18 show the results from a test regarding the efficacy of solutions containing Cocamide DEA formulation B and/or fatty acid esters against red mites. In the test, the red mites were placed in the tea bag and the top sealed with a paper clip or a staple. The teat bags were then submerged in solutions identified in FIGS. 16 and 17, and listed below and then hung up to dry. The mites are not removed from the bag but they are examined under a microscope and given a prod to stimulate them into movement if they are static. The number of dead mites is recorded, and FIGS. 16 and 17 represent the percentage of mites killed after exposure to each solution.

The solutions represented in FIG. 16 are as follows:

NG 1:3—7.5% Cocamide DEA formulation B and water to balance;

C—7% Cocamide DEA formulation B, 2% PEG-20, 3% lauric acid methyl ester and water to balance;

D—5% lauric acid methyl ester, 8% PEG-20 and water to balance; and

Control—8% PEG-20 and water to balance.

The solutions represented in FIG. 17 are as follows:

C8—1% Caprylic acid methyl ester and water to balance;
C9—1% Nonanoic acid methyl ester and water to balance;
C10—1% Capric acid methyl ester and water to balance;
C11—1% Undecaonoic acid methyl ester and water to balance;
C12—1% Lauric acid methyl ester and water to balance;
C13—1% tridecanoic acid methyl ester and water to balance;
C18—1% stearic acid methyl ester and water to balance;
C19—1% nonadecanoic acid ethyl ester and water to balance; and
Control—8% PEG-20 and water up to 100%.

The solutions represented in FIG. 18 are as follows:

Vial C—7% Cocamide DEA formulation B, 2% PEG-20, 3% lauric acid methyl ester and water to balance, and then diluted further with 50% additional water;

Vial D—5% Lauric acid methyl ester, 8% PEG-20@ and water to balance, and then further diluted with 50% additional water.

NG 1:4-5% Cocamide DEA formulation B and water to balance;
NG 1:6-2% Cocamide DEA formulation B and water to balance;
NG 1:8-0.5% Cocamide DEA formulation B and water to balance;
NG 1:10-0.175% Cocamide DEA formulation B and water to balance;
Octanoic acid—0.1% Octanoic acid and water to balance;
Methyl undecanoate—0.1% Methyl undecanoate and water to balance;
Methyl laurate—0.1% Laurie acid methyl ester and water to balance;
Ethyl dodecanoate—0.1% Ethyl dodecanoate and water to balance.

Example XV

Figure 19:
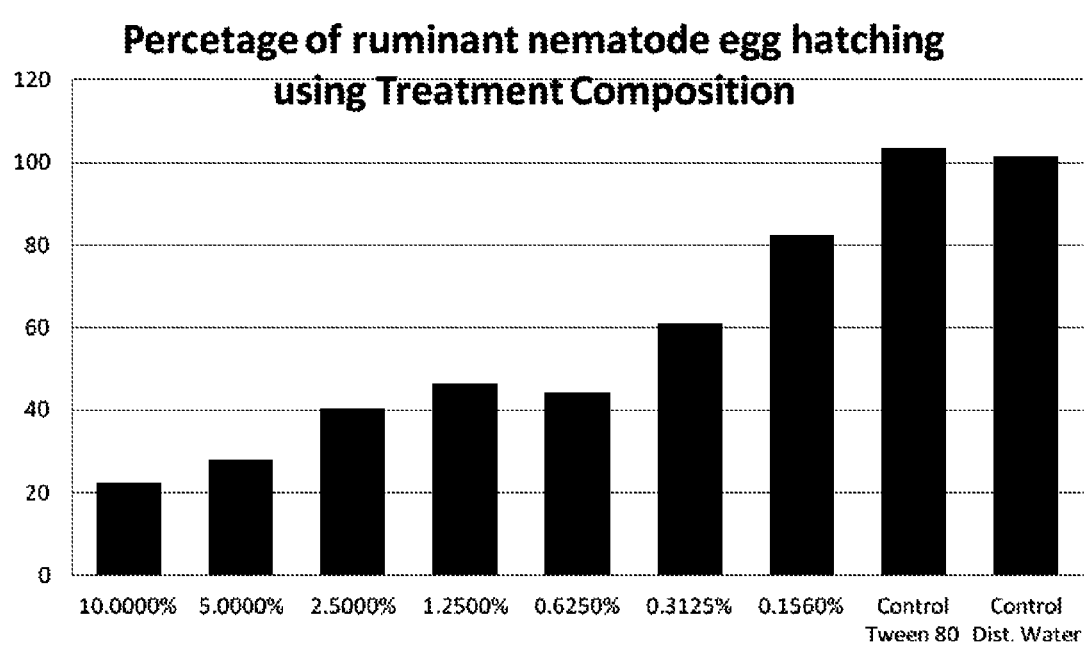
FIG. 19 shows a chart with results showing the percentage of ruminant nematode (*haemonchus*) egg hatching using various concentrations of a treatment composition according to the present invention.

FIG. 19 shows the results from an egg hatch test for nematode eggs, in particular *haemonchus* eggs, on cattle. In an experiment, *haemonchus* eggs derived from cattle were placed in increasing concentrations of the treatment composition of Table 12. The eggs were left for 24 hours in an incubator to hatch and then the number of hatched eggs was counted. Table 15 shows the results from the test, the results shown in FIG. 19 are the mean (average) results.

TABLE 15

Egg Hatch Test Results for Nematode (haemonchus) on Cattle

| Concentration | 1 | 2 | 3 | Mean |
|---|---|---|---|---|
| 10.0000% | 26 | 18 | 23 | 22.33333 |
| 5.0000% | 14 | 39 | 31 | 28 |
| 2.5000% | 47 | 36 | 38 | 40.33333 |
| 1.2500% | 42 | 46 | 51 | 46.33333 |
| 0.6250% | 40 | 55 | 38 | 44.33333 |
| 0.3125% | 59 | 67 | 57 | 61 |
| 0.1560% | 78 | 84 | 85 | 82.33333 |
| Control Tween 80 | 110 | 104 | 96 | 103.3333 |
| Control Dist. Water | 101 | 112 | 91 | 101.3333 |

It is to be understood that all of the present figures, and the accompanying narrative discussions of corresponding embodiments, do not purport to be completely rigorous treatments of the invention under consideration. It is to be understood that the above-described arrangements are only illustrative of the application of the principles of the present invention. Numerous modifications and alternative arrangements may be devised by those skilled in the art without departing from the scope of the present invention.

What is claimed is:

1. A composition, comprising:
   between 10-60% by weight of water based upon the weight of the composition;
   between 5-50% by weight of an active component based upon the weight of the composition, wherein the active component comprises esterified fatty acids in an amount of about 8-15% of the active component, at least one amide in an amount of about 80% or more of the active component, and a free amine radical amount of 1.5% or less of the active component;
   between 5-50% by weight of polyethylene glycol based upon the weight of the composition;
   between 5-50% by weight of at least one surfactant based upon the weight of the composition;
   between 5-35% by weight of at least one alcohol based upon the weight of the composition;
   between 0.1-5% by weight of at least one preservative based upon the weight of the composition; and
   optionally at least one buffering agent.

2. The composition according to claim 1, wherein the esterified fatty acids are from coconut oil.

3. The composition according to claim 2, wherein esterified fatty acids from coconut oil are fatty acid methyl esters, and the fatty acid methyl esters are is selected from any one of C8 to C18 fatty acid methyl esters from a group consisting of lauric acid methyl ester, oleic acid methyl ester, palmitic acid methyl ester, myristic acid methyl ester, capric acid methyl ester, linoleic acid methyl ester, stearic acid methyl ester and mixtures thereof.

4. The composition according to claim 1, further comprising at least one stabilizer, and at least one conditioning agent.

5. The composition according to claim 4, wherein the at least one stabilizer is selected from a group consisting of PEG-120 methyl glucose dioleate, Distearate-75 IPDI, xanthan gum and acadia gum;
   wherein the at least one conditioning agent is selected from a group consisting of phenyl trimethicone, cetrimonium chloride, stearamidopropyl dymethylamine, hydrolyzed wheat protein and Polyquaternium-7;
   wherein the composition further comprises:
   about 10% of a second alcohol by weight based upon the weight of the composition; and up to 5% by weight of at least one emulsifier based upon the weight of the composition;
- wherein the at least one stabilizer is between 2-6% by weight based upon the weight of the composition;
- wherein the at least one conditioning agent is between 2-6% by weight based upon the weight of the composition;
- wherein the second alcohol is selected from a group consisting of benzyl alcohol, ethanol, isopropanol and mixtures thereof; and
- wherein the at least one emulsifier is selected from a group consisting of polysorbate, disodium cetearyl sulfosuccinamate and mixtures thereof.

6. The composition according to claim 5, wherein the composition is a spray shampoo configured for use in any one or more of treatment or removal of lice, nit glue, lice eggs and blood sucking insects and as a solvent for nit glue.

7. The composition according to claim 1, wherein the composition is any one of a shampoo, a spray and a gel, and configured for use in any one or more of treatment or removal of any one or more of lice, nit glue, lice eggs and blood sucking insects and as a nit glue solvent.

8. The composition according to claim 1, wherein the active component comprises a coconut diethanolamide.

9. The composition according to claim 1, wherein the composition further comprises about 25% by weight of water, about 30% by weight of the active component and about 30% by weight of polyethylene glycol by weight based upon the weight of the total composition;
- wherein the at least one surfactant comprises sodium methyl cocoyl taurate and sodium laureth sulfate, and the sodium methyl cocoyl taurate comprises about 6% by weight of the composition based upon the weight of the total composition and the sodium laureth sulfate comprises about 2% by weight of the composition based upon the weight of the total composition;
- wherein the at least one alcohol comprises propanediol, and the propanediol comprises about 5% by weight of the composition based upon the weight of the total composition;
- wherein the at least one preservative comprises cocamidopropyl PG dimonium chloride phosphate, and cocamidopropyl PG dimonium chloride phosphate comprises about 1% by weight of the composition based upon the weight of the total composition; and
- wherein the at least one buffering agent comprises citric acid, and the citric acid comprises about 1% by weight of the composition based upon the weight of the total composition.

10. The composition according to claim 1, wherein the polyethylene glycol is selected from a group consisting of octaethylene glycol, PEG-6, glyceryl ether benzoate, isobudecyl ether, glyceryl ether lactate, PEG-10, PEG-19 and PEG-20;
- wherein the at least one surfactant is selected from a group consisting of sodium methyl cocoyl taurate, sodium laureth sulfate, sodium lauryl sulfate, ammonium lauryl sulfate, cocamidopropyl betaine, sodium cocoyl taurate and disodium cetearyl sulfosuccinamate;
- wherein the at least one alcohol is selected from a group consisting of ethanol, propandiol, pentylene glycol, propylene glycol, butylene glycol, benzyl alcohol and isopropanol;
- wherein the at least one buffering agent is selected from a group consisting of citric acid, lactic acid, phosphoric acid, sodium hydroxide and triethanolamine;
- wherein the at least one preservative is selected from a group consisting of cocamidopropyl PG dimonium chloride phosphate, sorbic acid, methylparaben, phenoxyethanol, chlorphenesin, potassium sorbate, sodium benzoate and sodium alginate.

11. The composition according to claim 1, wherein the composition further comprises 0.5% or less by weight of at least one fragrance based upon the total weight of the composition; and 0.5% or less by of at least one coloring agent based upon the total weight of the composition.

12. The composition according to claim 1, wherein the composition further comprises:
- between 2-4% of acrylates copolymer by weight based upon the weight of the composition;
- between 2-6% of Polyquaternium-7 by weight based upon the weight of the composition;
- at least one stabilizer between 2-6% by weight based upon the weight of the composition; and
- at least one conditioning agent between 2-6% by weight based upon the weight of the composition.

13. A composition, comprising:
- between 10-90% by weight of water based upon the weight of the composition;
- between 2-25% by weight of an active component based upon the weight of the composition;
- up to about 5% by weight of at least one stabilizer based upon the weight of the composition;
- optionally at least one buffering agent; and
- optionally between 0.1-0.5% by weight of at least one fragrance based upon the total weight of the composition;
- such that the active component comprises a coconut diethanolamide having at least one amide in an amount of at least 80% by weight of the active component, esterified fatty acids from coconut oil in an amount between 8-15% by weight of the active component and a free amine radical amount of 1.5% or less by weight of the active component, and
- in which the esterified fatty acids from the coconut oil are fatty acid methyl esters.

14. The composition according to claim 13, wherein the fatty acid methyl esters are selected from any one of C8 to C18 fatty acid methyl esters from a group consisting of lauric acid methyl ester, unsaturated oleic acid methyl ester, palmitic acid methyl ester, myristic acid methyl ester, capric acid methyl ester, linoleic acid methyl ester, stearic acid methyl ester and mixtures thereof.

15. The composition according to claim 14, wherein the composition is for one or more of repellence of insects, soothing of insect bites, superficial burns, skin wounds, and healing of insect bites.

16. The composition according to claim 13, wherein the at least one buffering agent is selected from a group consisting of citric acid, lactic acid, phosphoric acid, sodium hydroxide, triethanolamine and mixtures thereof; and
- wherein the at least one stabilizer is selected from a group consisting of PEG-120 methyl glucose dioleate, Distearate-75 IPDI, xanthan gum, acadia gum and mixtures thereof.

17. A composition, comprising:
- between 70-90% by weight of water based upon the weight of the composition;
- between 2-20% by weight of an active component;
- about 2% by weight of cocamidepropyl PG dimonium chloride phosphate based upon the total weight of the composition;

about 1% by weight of at least one buffering agent based upon the total weight of the composition;

between 2-5% by weight of propanediol based upon the total weight of the composition; and between 2-5% by weight of at least one surfactant based upon the total weight of the composition;

such that the active component includes at least one amide in an amount of at least 80% by weight of the active component, esterified fatty acids in an amount between 8-15% by weight of the active component and a free amine radical amount of 1.5% or less by weight of the active component, and in which esterified fatty acids of the active component are from a coconut oil.

18. The composition according to claim 17, wherein the esterified fatty acids from coconut oil are fatty acid methyl esters, and the fatty acid methyl esters are is selected from any one of C8 to C18 fatty acid methyl esters from a group consisting of lauric acid methyl ester, unsaturated oleic acid methyl ester, palmitic acid methyl ester, myristic acid methyl ester, capric acid methyl ester, linoleic acid methyl ester, stearic acid methyl ester and mixtures thereof, and wherein the active component comprises a coconut diethanolamide.

19. The composition according to claim 18, wherein the composition is for one or more of repellence of insects, soothing of insect bites, superficial burns, skin wounds, and healing of insect bites.

20. The composition according to claim 17, wherein the composition is configured for use in aiding in the treatment, repellance and/or killing of bed bugs, flies, and/or fleas.

21. The composition according to claim 17, wherein the composition is configured for use in effecting ovicidal activity on animal nematodes and haemonchus.

22. The composition according to claim 17, wherein the at least one buffering agent is selected from a group consisting of citric acid, lactic acid, phosphoric acid, sodium hydroxide, triethanolamine or mixtures thereof;

wherein the at least one surfactant is selected from a group consisting of sodium methyl cocoyl taurate, sodium laureth sulfate, sodium lauryl sulfate, ammonium lauryl sulfate, cocamidopropyl betaine, sodium cocoyl taurate, disodium cetearyl sulfosuccinamate and mixtures thereof.

23. A composition, comprising:

between 75-95% of water by weight based upon the weight of the composition;

less than 5% by weight of an active component comprising esterified fatty acids based upon the weight of the composition, wherein fatty acids for the esterified fatty acids are any one or more of medium chain fatty acids having carbon chains from C6 to C12; and at least one emulsifier, wherein the emulsifier is a different component than the active component.

24. The composition according to claim 23, wherein the composition includes at least one of the group consisting of a fragrance and a preservative.

25. The composition according to claim 23, wherein the esterified fatty acids are selected from the group consisting of fatty acid methyl esters, fatty acid ethyl esters, fatty acid propyl esters and fatty acid isopropyl esters and mixtures thereof.

26. The composition according to claim 23, wherein the composition further comprises a mixture in an amount between 5-50% by weight that comprises diethanolamide and at least one coconut oil fatty acid methyl ester, wherein the amount of the at least one coconut oil fatty acid methyl ester in the mixture is between 8-15% by weight of the mixture, the amount of the diethanolamide in the mixture is at least 80% by weight of the mixture, and the amount of a free amine in the mixture is 1.5% or less by weight of the mixture, wherein the diethanolamide has undergone a purification process to lower the amount of the free amine, increase the amount of the coconut oil fatty acid methyl esters, and change fatty acid methyl ester characteristics.

27. The composition according to claim 23, wherein the esterified fatty acids are lauric acid esters.

28. The composition according to claim 23, wherein the composition is configured for use as one or more of a pesticide, insecticide and insect repellant.

29. The composition according to claim 23, wherein the composition is configured for aiding in the healing of infections, irritations, scratches, cuts, abrasions and burns.

30. The composition according to claim 23, wherein the composition is configured for internal and external use in killing, removing and/or repelling endoparasites and/or ectoparasites, including bacteria, protozoa pathogens, fungi and virus.

31. A composition, comprising:

between 65-95% by weight of water based on the weight of the composition;

between 0.1-30% by weight of an active component based on the weight of the composition, the active component comprising at least one amide in an amount of at least 80% by weight of the active component, esterified fatty acids from coconut oil in an amount of between 8-15% by weight of the active component, and a free amine radical amount of 1.5% or less by weight of the active component;

between 0.001-5% by weight of fatty acid esters based on the weight of the composition, the fatty acid esters selected from medium chain fatty acids having one or more carbon chains between C6 to C12; and between 5-20% by weight of an emulsfier.

32. The composition according to claim 31, wherein the fatty acid esters are lauric acid esters.

33. The composition according to claim 31, wherein the composition is configured for use in any one or more of an internal or external use for and one of killing and repelling insects and parasites.

34. The composition according to claim 31, wherein the esterified fatty acids from coconut oil are fatty acid methyl esters, and the fatty acid methyl esters are selected from one or more of a C8 to C18 fatty acid methyl ester consisting of lauric acid methyl ester, unsaturated oleic acid methyl ester, palmitic acid methyl ester, myristic acid methyl ester, capric acid methyl ester, linoleic acid methyl ester, stearic acid methyl ester and mixtures thereof.

* * * * *